US011925697B2

United States Patent
Klee et al.

(10) Patent No.: US 11,925,697 B2
(45) Date of Patent: Mar. 12, 2024

(54) DENTAL IMPRESSION MATERIAL

(71) Applicant: DENTSPLY DETREY GMBH, Constance (DE)

(72) Inventors: Joachim Klee, Radolfzell (DE); Florian Szillat, Constance (DE); Maximilian Maier, Dusseldorf (DE); Marjorie Yon, Villelongue de la Salanque (FR); Jacques Lalevée, Mulhouse (FR); Julie Kirschner, Dambachla-Ville (FR); Fabrice Morlet-Savary, Pfastatt (FR); Céline Dietlin, Mulhouse (FR)

(73) Assignee: DENTSPLY SIRONA INC., York, PA (US)

( * ) Notice: Subject to any disclaimer, the term of this patent is extended or adjusted under 35 U.S.C. 154(b) by 814 days.

(21) Appl. No.: 16/982,094

(22) PCT Filed: Mar. 7, 2019

(86) PCT No.: PCT/EP2019/055730
§ 371 (c)(1),
(2) Date: Sep. 18, 2020

(87) PCT Pub. No.: WO2019/170811
PCT Pub. Date: Sep. 12, 2019

(65) Prior Publication Data
US 2021/0106503 A1 Apr. 15, 2021

(30) Foreign Application Priority Data
Mar. 7, 2018 (EP) ..................................... 18160497

(51) Int. Cl.
*A61K 6/90* (2020.01)
*A61C 13/15* (2006.01)
*A61C 9/00* (2006.01)

(52) U.S. Cl.
CPC .............. *A61K 6/90* (2020.01); *A61C 19/003* (2013.01); *A61C 9/0006* (2013.01)

(58) Field of Classification Search
CPC ...... A61C 19/003; A61C 19/0006; A61K 6/90
(Continued)

(56) References Cited

U.S. PATENT DOCUMENTS

| 4,361,528 A | * | 11/1982 | Ginsburg | ............. A61C 9/0006 264/16 |
| 5,155,252 A | * | 10/1992 | Yamamoto | ............. C07C 69/54 526/321 |

(Continued)

FOREIGN PATENT DOCUMENTS

| EP | 170219 A | * | 2/1986 | ............... A61C 9/00 |
| EP | 3231413 A1 | * | 10/2017 | ........... A61K 6/0038 |

OTHER PUBLICATIONS

Novakov, et al.; "Peculiarities of the production of materials based on polysulfide oligomer-polymerizable compound compositions cured in the presence of manganese oxide"; Polymer Science Series D; Glues and Sealing Materials; vol. 5, No. 2; May 2012; pp. 96-101.

*Primary Examiner* — Matthew M Nelson
(74) *Attorney, Agent, or Firm* — DENTSPLY SIRONA INC.

(57) ABSTRACT

A photocurable dental impression material comprising:
(a) a mixture of polymerizable silicone compounds each having two or more polymerizable (meth)acrylate groups, said mixture having a dynamic viscosity at 25° C. of from 1 to 100 Pas;
(b) a filler;
(c) a photo initiator system,
wherein the mixture of polymerizable silicone compounds comprises based on the total weight of the mixture of polymerizable silicone compounds
(Continued)

(a) 10 to 90 percent by weight of high-molecular polymerizable silicone compounds having a molecular weight in the range of from more than 4000 up to 10.000; and
(b) 90 to 10 percent by weight of polymerizable silicone compounds having a molecular weight in the range of from 300 to 4000.

18 Claims, 7 Drawing Sheets

(58) Field of Classification Search
USPC .......................................................... 433/37
See application file for complete search history.

(56) References Cited

U.S. PATENT DOCUMENTS

2016/0128911 A1* 5/2016 Fontein .................. A61K 6/887
523/116
2021/0106503 A1* 4/2021 Klee .................... A61C 19/003

* cited by examiner

DENTAL IMPRESSION MATERIAL

FIELD OF THE INVENTION

The present invention relates to a photocurable dental impression material. Moreover, the present invention relates to a method for preparing a dental impression. Finally, the present invention relates to a use of the curable dental impression material of the present invention for the preparation of a dental impression.

BACKGROUND OF THE INVENTION

Dental impression materials are known. Dental impression materials are commonly available as reactive multi-component materials provided in packages including two compartments or two separate containers that keep the components isolated from each other during storage. Once the components are mixed, a chemical reaction is initiated that turns the mixed composition into a hardened mass during the setting time. Moreover, the working time and the setting time of conventional dental impression materials are limited and depend on the rate of the curing reaction. Therefore, storage stability of a dental impression material depends on the separation of reactive components and necessitates mixing prior to use which needs to be done chairside immediately prior to use so that the dental impression may be completed during the working time of usually only a few minutes.

In view of the stability-reactivity problems inherent in conventional dental impression materials, devices have been developed for the automatic mixing and dispensing of dental impression materials in order to provide high precision with regard to the homogeneity of the mixture, and the ratio of the two components to be mixed. Accordingly, the components of the dental impression material are simultaneously supplied from separate material chambers to a mixer during application of the dental impression material, which mixes and then dispenses a mixed paste. The paste may be supplied from the mixer directly onto a dental impression tray for immediate placement in a patient's mouth.

Once the material components have come into contact with each other in the mixing chamber, the mixture of the material in the mixing chamber can only be stored for a short time because the mixed material will soon set inside the mixing chamber unless dispensed and used. Therefore, the dental practitioner may have to remove and replace mixers several times each day.

Dental impression materials may be silicone impression material curable in an addition or condensation reaction whereby addition silicones are most popular. Although conventional addition silicone impression materials provide good detail reproduction, excellent dimensional stability, little shrinkage on set, addition silicones are inherently hydrophobic and as such require moisture control for optimal use. Finally, addition silicones have only a poor tear resistance.

U.S. Pat. No. 5,137,448 discloses a dental impression composition that is polymerizable by having an initiator activated by actinic light within the visible light range of 360 to 600 nanometers, which contains a compound having at least two terminal acrylate unsaturations and an organosilicone containing backbone.

CA-A 2 296 227 discloses dental materials which contain polymerizable polysiloxane compounds.

EP-A 0 170 219 discloses a method of curing a dental impression material by passing actinic light through a tray while the tray is in contact with the impression making composition. Moreover, EP-A 0 170 219 discloses a dental impression composition that is polymerizable by having an initiator activated by actinic light within the visible light range of 360 to 600 nanometers, which comprises a compound having at least two terminal acrylate unsaturations and an organosilicone containing backbone.

SUMMARY OF THE INVENTION

It is the problem of the present invention to provide a dental impression material which is highly tolerant to moisture, which has adjustable working and setting times, and which has excellent tear resistance while providing at the same time good detail reproduction, excellent dimensional stability, and no shrinkage on set, and which may be provided as a single composition which does not need mixing prior to use.

Moreover, it is the problem of the present invention to provide a method for preparing a dental impression which does not require strict moisture control, wherein working and setting times may be determined by the dental practitioner, whereby the dental impression material has excellent tear resistance and provides at the same time good detail reproduction, excellent dimensional stability, and reduced shrinkage on set.

Finally, it is the problem of the present invention to provide a use of the dental impression material of the present invention.

The present invention provides a photocurable dental impression material comprising:
(a) a mixture of polymerizable silicone compounds each having two or more polymerizable (meth)acrylate groups, said mixture having a dynamic viscosity at 25° C. of from 1 to 100 Pas;
(b) a filler;
(c) a photo initiator system,
wherein the mixture of polymerizable silicone compounds comprises based on the total weight of the mixture of polymerizable silicone compounds
(I) 10 to 90 percent by weight of high-molecular polymerizable silicone compounds having a molecular weight in the range of from more than 4000 up to 10.000; and
(ii) 90 to 10 percent by weight of polymerizable silicone compounds having a molecular weight in the range of from 300 to 4000.

Moreover, the present invention provides a method for preparing a dental impression, which method comprises
(a) providing a curable dental impression material of the present invention;
(b) taking an impression of a dental structure;
(c) curing the dental impression material with light having a wavelength in the range of 200 to 800 nm.

Finally, the present invention provides a use of the curable dental impression material of the present invention for the preparation of a dental impression.

The present invention is based on the recognition that a specific mixture of radically polymerizable silicone compounds adjusted in a dynamic viscosity range of 1 to 100 Pas may be used in a filled dental impression material for photocuring. Accordingly, it is possible to provide a one component composition which has high storage stability and which does not require mixing prior to use. At the same time, the dental impression material provides when cured excellent tear resistance, good detail reproduction, excellent dimensional stability, and no shrinkage on set.

BRIEF DESCRIPTION OF THE FIGURES

FIG. 3 shows depth of cure for the polymerization upon blue light (SmartLite Focus; under Air) of (A) CN9800/ BMTMDS (70%/30% w/w) using CQ/Speedcure 938/ DMABN (1%/1%1% w/w) as photoinitiating system (100 s of irradiation); (B) CN9800/BMTMDS (70%/30% w/w) using CQ/Speedcure 938/DMABN (0.5/1/1% w/w) as photoinitiating system (100 s of irradiation); (C) CN9800/ BMTMDS (70%/30% w/w) using CQ/Speedcure 938/ DMABN (0.6/1/1% w/w) as photoinitiating system (100 s of irradiation) in presence of silica fillers (SDI Glass; 10% w/w).

DETAILED DESCRIPTION OF THE PREFERRED EMBODIMENTS

Figure 1:
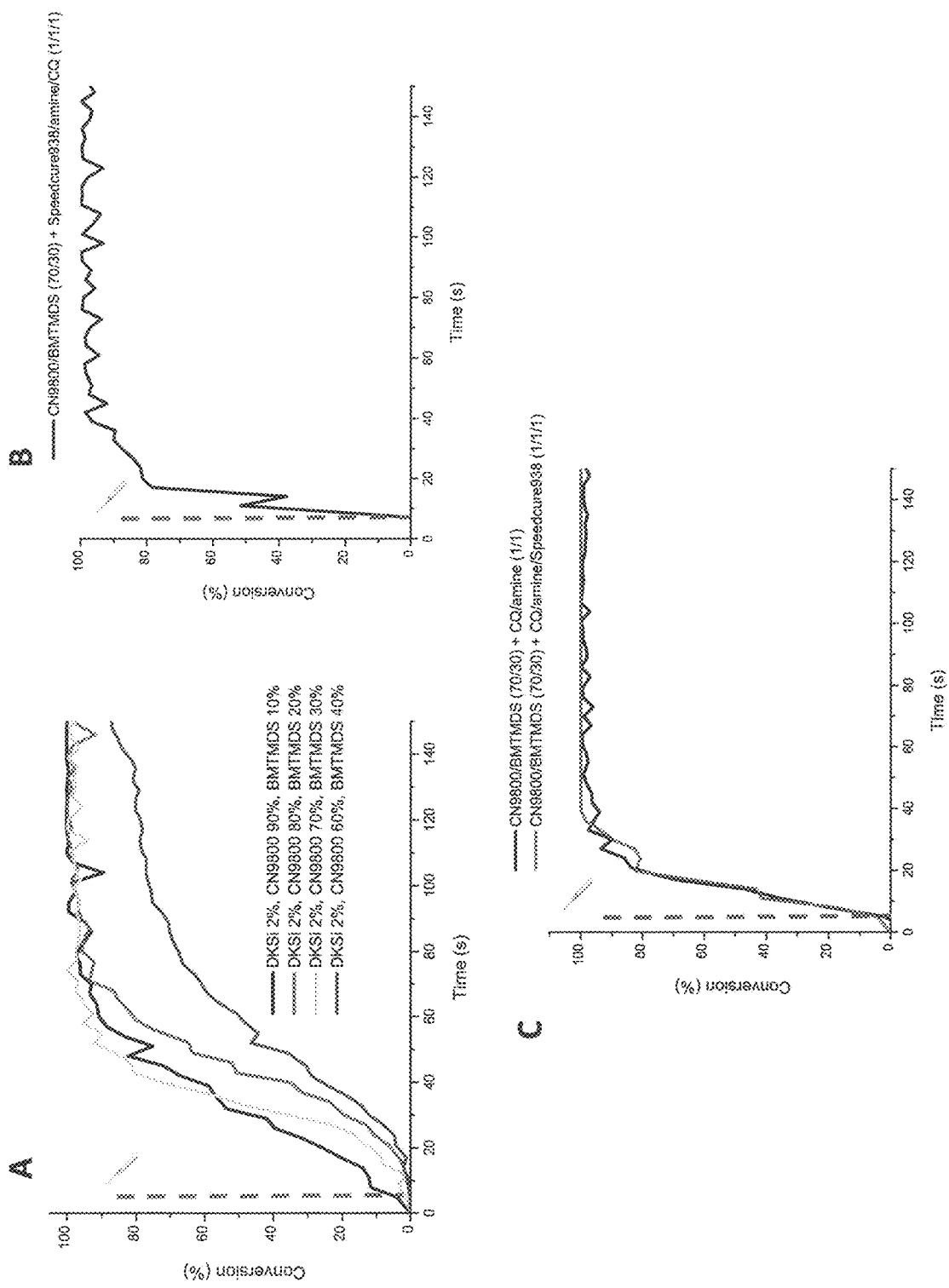
FIG. 1 shows photopolymerization profiles of (meth) acrylate function for (A) different CN9800/BMTMDS blend (% w/w) using DKSi 2% (w/w) as photoinitiating system; (B) CN9800/BMTMDS (70%/30% w/w) using CQ/DMABN/Speedcure 938 (1/1/1 w/w) and (C) CN9800/ BMTMDS (70%/30% w/w) using CQ/DMABN/Speedcure 938 (1/1/1% w/w) or CQ/DMABN (1/1% w/w) (under air; thickness=1.4 mm; Smartlite Focus 300 mW·cm$^{-2}$).

The terms "polymerization" and "polymerizable" relates to the combining or the capability to combine by covalent bonding of a large number of smaller molecules, such as monomers, to form larger molecules, that is, macromolecules or polymers. The monomers may be combined to form only linear macromolecules or they may be combined to form three-dimensional macromolecules, commonly referred to as crosslinked polymers. For example, monofunctional monomers form linear polymers, whereas monomers having at least two functional groups form crosslinked polymers also known as networks.

The terms "photocurable" and "curable" refer to a dental composition that will polymerize into a polymer network when irradiated for example with actinic radiation such as ultraviolet (UV), visible, or infrared radiation.

"Actinic radiation" is any electromagnetic radiation that is capable of producing photochemical action and can have a wavelength of at least 150 nm and up to and including 1250 nm, and typically at least 300 nm and up to and including 750 nm.

The term "coinitiator" refers to a molecule that produces a chemical change in another molecule such as an initiator of formulae (I) to (IV). The coinitiator may for example be selected from the group consisting of a compound having a Si—H or Ge—H bond, an electron donor such as an amine or phosphine compound, and a carbazole compound.

The term "electron donor" as used herein means a compound capable of contributing electrons in a photochemical process. Suitable examples include organic compounds having heteroatoms with electron lone pairs, for example amine compounds.

The present invention provides a photocurable dental impression material. The photocurable dental impression material is preferably a one-pack composition packaged in a syringe or provided on a ready-to-use dental impression tray. Alternatively, the photocurable dental impression material of the present invention may also be a two-pack composition, in particular when formulated as a dual cure composition containing an additional redox initiator system.

When packaged in a syringe or provided on a ready-to-use dental impression tray, the composition must be shielded from actinic light during storage.

The Mixture of Polymerizable Silicone Compounds

The dental impression material of the present invention comprises a mixture of polymerizable silicone compounds each having two or more polymerizable (meth)acrylate groups, said mixture having a dynamic viscosity at 25° C. of from 1 to 100 Pas. Preferably, said mixture having a dynamic viscosity at 25° C. of from 5 to 80 Pas, more preferably from 10 to 70 Pas. The dynamic viscosity is a measure of the internal resistance of a fluid to flow. In the SI system the dynamic viscosity is expressed in Pa·s. The dynamic viscosity can be measured with various types of viscometers and rheometers, for example a Bohlin CS50 rheometer, at a temperature of 25° C.

The mixture of polymerizable silicone compounds comprises based on the total weight of the mixture of polymerizable silicone compounds (a) 10 to 90 percent by weight of high-molecular polymerizable silicone compounds having a molecular weight in the range of from more than 4000 up to 10.000 Da; and (b) 90 to 10 percent by weight of polymerizable silicone compounds having a molecular weight in the range of from 300 to 4000.

Preferably, the mixture of polymerizable silicone compounds comprises based on the total weight of the mixture of polymerizable silicone compounds (a) 20 to 80 percent by weight of high-molecular polymerizable silicone compounds having a molecular weight in the range of from more than 4000 up to 10.000 Da; and (b) 80 to 20 percent by weight of polymerizable silicone compounds having a molecular weight in the range of from 300 to 4000.

According to a further preferred embodiment, the mixture of polymerizable silicone compounds comprises based on the total weight of the mixture of polymerizable silicone compounds
(a) 25 to 75 percent by weight of high-molecular polymerizable silicone compounds having a molecular weight in the range of from more than 4000 up to 10.000 Da; and
(b) 75 to 25 percent by weight of polymerizable silicone compounds having a molecular weight in the range of from 300 to 4000.

According to a further preferred embodiment, the mixture of polymerizable silicone compounds comprises based on the total weight of the mixture of polymerizable silicone compounds
(a) 50 to 85 percent by weight of high-molecular polymerizable silicone compounds having a molecular weight in the range of from more than 4000 up to 10.000 Da; and
(b) 15 to 50 percent by weight of polymerizable silicone compounds having a molecular weight in the range of from 300 to 4000.

According to a further preferred embodiment, the mixture of polymerizable silicone compounds comprises based on the total weight of the mixture of polymerizable silicone compounds
(a) 55 to 85 percent by weight of high-molecular polymerizable silicone compounds having a molecular weight in the range of from more than 4000 up to 10.000 Da; and
(b) 15 to 45 percent by weight of polymerizable silicone compounds having a molecular weight in the range of from 300 to 4000.

According to a further preferred embodiment, the mixture of polymerizable silicone compounds comprises based on the total weight of the mixture of polymerizable silicone compounds
(a) 60 to 85 percent by weight of high-molecular polymerizable silicone compounds having a molecular weight in the range of from more than 4000 up to 10.000 Da; and
(b) 15 to 40 percent by weight of polymerizable silicone compounds having a molecular weight in the range of from 300 to 4000.

The silicone compounds having a molecular weight in the range of from more than 4000 up to 10.000 Da are organosilicone compounds having a higher molecular weight and a lower ratio of (meth)acrylate groups per total molecular weight of the molecule. Accordingly, an increase of the amount of such organosilicone compounds reduces the crosslinking density and thereby potentially the shrinkage and mechanical properties of the composition after curing.

The silicone compounds having a molecular weight in the range of from 300 to 4000 are organosilicone compounds having a lower molecular weight and a higher ratio of (meth)acrylate groups per total molecular weight of the molecule. Accordingly, an increase of the amount of such organosilicone compounds increases the crosslinking density and thereby potentially the shrinkage and mechanical properties of the composition after curing. Given that the dynamic viscosity of the silicones according to (b) is lower than the dynamic viscosity of the silicones according to (a), an increase of the amount of the silicones according to (b) reduces the overall viscosity and may be used to adjust the dynamic viscosity at 25° C. of the mixture to 1 to 100 Pas.

According to a preferred embodiment, the silicone compounds having a molecular weight in the range of from 300 to 4000 are organosilicone compounds having a molecular weight of at most 3000, more preferably at most 2000.

Preferably, the polymerizable silicone compounds are compounds of the following formula (I):

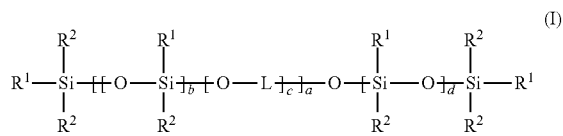

In a compound of formula (I), at least two (meth)acrylate groups are present. The (meth)acrylate groups may be present at each terminal positions. Alternatively, the (meth)acrylate groups may be present at only one terminal position.

In a compound of formula (I), $R^1$ represents a (meth)acrylate group containing organic residue, a $C_{1-4}$ alkyl group, a group of the formula [—OSiR'$_2$]$_n$R', or two groups $R^1$ or a group $R^1$ and $R^2$ form together a group [—O-SiR'$_2$]$_n$—, wherein the R', which may be the same or different, independently represent a $C_{1-4}$ alkyl group or an (meth)acrylate group containing organic residue and n is an integer of from 1 to 20.

The (meth)acrylate group containing organic residue may be an organic residue having from 1 to 45 carbon atoms, which is substituted by 1 to 3 (meth)acrylate groups, and whereby the organic residue may contain 1 to 14 heteroatoms selected from oxygen, nitrogen and sulphur. Preferably, the divalent organic residue is a linear $C_{1-18}$ or branched $C_{3-18}$ alkyl group or $C_2$ to $C_{18}$ alkenyl group which may contain 1 to 6 heteroatoms selected from oxygen, nitrogen and sulphur.

Preferably, $R^1$ is a group of the following formula (II)

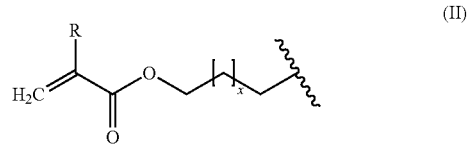

In a compound of formula (II), R represents a hydrogen atom or a methyl group. Moreover, x is 0 or an integer of from 1 to 8. Preferably, x is 0, 1 or 2.

In case $R^1$ is not a (meth)acrylate group containing organic residue, then $R^1$ is preferably a methyl group or an ethyl group.

In a compound of formula (I), $R^2$ represents a $C_{1-4}$ alkyl group or a group of the formula [—OSiR''$_2$]$_m$R'', or two groups $R^2$ or a group $R^1$ and $R^2$ form together a group [—OSiR''$_2$]$_m$—, wherein the R'', which may be the same or different, independently represent a $C_{1-4}$ alkyl group and m is an integer of from 1 to 20. Most preferably, $R^2$ is a methyl group or an ethyl group.

In a compound of formula (I), L represents a divalent $C_{1-20}$ organic linker group. In particular, the linker group L may be a hydrocarbon group which may be aliphatic and/or aromatic. A $C_{1-20}$ organic linker group may contain 1 to 8 heteroatoms selected from oxygen, nitrogen and sulphur, which divalent organic residue may be substituted with one or more substituents selected from the group consisting of a $C_{1-4}$ alkoxy groups, a hydroxyl group, a thiol group, and a $C_{6-14}$ aryl group. L may be a linear or branched group. The hydrocarbon group may be substituted by 1 to 6 $C_{1-4}$ alkyl groups. Specific examples of the alkyl groups are methylene, ethylene, n-propylene, i-propylene, n-butylene, i-butylene or tert.-butylene. In a preferred embodiment, the hydrocarbon group of the linker group L may contain 1 to 5 oxygen atoms in the hydrocarbon group in the form of aliphatic or aromatic ether bonds, keto groups, carboxylic acid groups, or hydroxyl groups. In case of an aliphatic group, L may be a straight chain or branched chain alkylene group or a cycloalkylene group. In case of an aromatic group, A may be an arylene group or a $C_{3-14}$ heteroarylene group. Specifically, L may be a divalent substituted or unsubstituted $C_{1-20}$ alkylene group, substituted or unsubstituted $C_{6-14}$ arylene group, substituted or unsubstituted $C_{3-20}$ cycloalkylene group, substituted or unsubstituted $C_{7-20}$ arylenealkylenearylene group.

According to a preferred embodiment, L represents a saturated aliphatic 02-20 hydrocarbon chain which may contain 2 to 4 oxygen atoms or nitrogen atoms, and which may be substituted by 1 to 6 $C_{1-4}$ alkyl groups, or L may be a substituted or unsubstituted $C_{7-20}$ arylenealkylenearylene group which may be substituted by 1 to 6 $C_{1-4}$ alkyl groups.

In a compound of formula (I), a represents 0 or an integer of from 1 to 20.

In a compound of formula (I), b represents 0 or an integer of from 1 to 20;

In a compound of formula (I), c represents 0 or an integer of from 1 to 20;

In a compound of formula (I), d represents 0 or an integer of from 1 to 20.

According to a preferred embodiment, the mixture of polymerizable silicone compounds each having two or more polymerizable (meth)acrylate groups comprises 1,3-bis(3-methacryloxypropyl)tetramethyldisiloxane (BMTMDS), 1,3-bis(3-methacyloxypropyl)tetrakis(trimethylsiloxy)disiloxane, methacryloxypropyl terminated polydimethylsiloxane, CN9800 (Sartomer), and or PRO21536 (Sartomer). CN9800 is an aliphatic silicone acrylate having a viscosity of 20 to 60 Pa·s at 25° C.

Preferably, the dental impression material comprises 40 to 90 percent by weight, in particular 45 to 85 percent by weight, more preferably 50 to 80 percent by weight, based on the total weight of the dental impression material of mixture of polymerizable silicone compounds each having two or more polymerizable (meth)acrylate groups.

The Filler

The dental impression material of the present invention comprises a filler. The filler is a particulate filler which has preferably a mean particle size in the range of from 0.05 to 5 μm as measured, for example, by electron microscopy or by using a conventional laser diffraction particle sizing method as embodied by a MALVERN Mastersizer S or MALVERN Mastersizer 2000 apparatus. The particulate filler may be a multimodal particulate filler representing a mixture of two or more particulate fractions having different average particle sizes. The particulate reactive filler may also be a mixture of particles of different chemical composition.

Preferably, the photocurable dental impression material comprises 10 to 60 percent by weight, in particular 15 to 55 percent by weight, more preferably 20 to 50 percent by weight, based on the total weight of the dental impression material of a filler.

The specific type of filler is not particularly limited. Accordingly, any toxicologically acceptable inorganic, especially hydrophobic fillers may be employed such as silicas, aluminas, magnesias, titanias, inorganic salts, metallic oxides and glasses.

The filler may be a mixtures of different fillers such as silicone dioxides including crystalline forms, in particular particulate quartz, amorphous silicon dioxides, in particular diatomaceous earth, and silanated fumed silica.

The viscosity and thixotropicity of the uncured as well as the physical properties of the cured compositions may be controlled by varying the sizes and surface areas of the filler.

The filler may be surface treated with one or more silanating agents. Preferred silanating agents include those having at least one polymerizable double bond and at least one group that easily hydrolyses with water. Examples of such agents include 3-methacryloxypropyltrimethoxysilane, 3-methacryloxypropyldimethoxy-monochlorosilane, 3-methacryloxypropyldichloromonomethoxysilane, methacryloxypropyltri-chlorosilane, 3-methacryloxypropyldichloromonomethyl-silane, 3-methacryloxypropylmonochlorodimethylsilane, and mixtures thereof.

Preferred filler are fumed silica, quartz, cristobalite, calcium silicate, diatomaceous earth, zirconium silicate, montmorillonite such as bentonite, zeolite, including molecular sieves such as sodium aluminium silicate, metal oxide powder such as aluminium or zinc oxide or their mixed oxides, barium sulphate, calcium carbonate, plaster, and glass powder.

The Photo Initiator System.

The dental impression material of the present invention comprises a photo initiator system.

Any compound or system capable of initiating the polymerization of the mixture of polymerizable silicone compounds according to the present invention may be used as the photoinitiator system.

For example, a suitable photoinitiator system may be in the form of a binary or tertiary system. A binary systems may include a photoinitiator and an electron donor compound, and a tertiary system may include an iodonium, sulfonium or phosphonium salt, a photoinitiator, and an electron donor compound, as for example described in U.S. Pat. No. 5,545,676.

Suitable photoinitiators are monoketones and diketones that absorb some light within a range of about 400 nm to about 520 nm (preferably, about 450 nm to about 500 nm). Particularly suitable compounds include alpha diketones that have some light absorption within a range of about 400 nm to about 520 nm (even more preferably, about 450 to about 500 nm). Examples include camphor quinone, benzil, furil, 3,3,6,6-tetramethylcyclo-hexanedione, phenanthraquinone, 1-phenyl-1,2-propanedione and other 1-aryl-2-alkyl-1,2-ethanediones, and cyclic alpha diketones.

Moreover, suitable photoinitiators are compounds of the following formula (III) as disclosed in EP 3231413 A1 and EP 3153150 A1:

(III)

In a compound of formula (III), M is Ge or Si.

Moreover, in a compounds of formula (III), $R^3$, $R^4$ and $R^5$ may be the same or different, independently represent an organic group. Preferably, $R^3$ and $R^4$ independently from each other represent a substituted or unsubstituted hydrocarbyl or hydrocarbylcarbonyl group, and $R^5$ represents a substituted or unsubstituted hydrocarbyl group. The hydrocarbyl group may be an alkyl group, a cycloalkyl group, a cycloalkylalkyl group, an arylalkyl group or an aryl group. An alkyl group may be linear $C_{1-20}$ or branched $C_{3-20}$ alkyl group, typically a linear $C_{1-8}$ or branched $C_{3-8}$ alkyl group. Examples for $C_{1-16}$ alkyl groups can include linear or branched alkyl groups having 1 to 6 carbon atoms, preferably 1 to 4 carbon atoms, for example, methyl, ethyl, n-propyl, isopropyl, n-butyl, isobutyl, sec-butyl, tert-butyl, n-pentyl, isopentyl and n-hexyl. A cycloalkyl group may be a $C_{3-20}$ cycloalkyl group, typically a $C_{3-8}$ cycloalkyl group. Examples of the cycloalkyl group can include those having 3 to 6 carbon atoms, for example, cyclopropyl, cyclobutyl, cyclopentyl and cyclohexyl. A cycloalkylalkyl group may have 4 to 20 carbon atoms and may include a combination of a linear or branched alkyl group having 1 to 6 carbon atoms and a cycloalkyl group having 3 to 14 carbon atoms. Examples of the cycloalkylalkyl(-) group can for example, include methylcyclopropyl methylcyclobutyl, methylcyclopentyl, methylcyclohexyl, ethylcyclopropyl, ethylcyclobutyl, ethylcyclopentyl, ethylcyclohexyl, propylcyclopropyl, propylcyclobutyl, propylcyclopentyl, propylcyclohexyl. An arylalkyl group may be a $C_{7-20}$ arylalkyl group, typically a combination of a linear or branched alkyl group having 1 to 6 carbon atoms and an aryl group having 6 to 10 carbon atoms. Specific examples of an arylalkyl group are a benzyl group or a phenylethyl group. An aryl group can include aryl groups having 6 to 10 carbon atoms. Examples of the aryl group are phenyl and naphtyl.

The hydrocarbylcarbonyl groups of $R^3$ and $R^4$ represent acyl groups ($R_{org}$—(C=O)—) in which the organic residue $R_{org}$ is a hydrocarbyl residue as defined above.

Compound of formula (III) may contain one or two hydrocarbylcarbonyl groups, that is either one of $R^3$ and $R^4$ is a hydrocarbylcarbonyl group, or both $R^3$ and $R^4$ are hydrocarbylcarbonyl groups. Preferably, compound of formula (I) contains one hydrocarbylcarbonyl group. Preferably, the hydrocarbylcarbonyl group is an arylcarbonyl group, more preferably a benzoyl group. Preferably, $R^3$ and $R^4$ are independently selected from the group consisting of a linear $C_{1-6}$ or branched $C_3$-6 alkyl group, and a phenyl or benzoyl group which may optionally be substituted by one to three substitutents selected from halogen atoms, a nitro group, a $C_{1-4}$ alkoxy group and a —$NR^xR^y$ group wherein $R^x$ and $R^y$ independently from each other represent a $C_{1-4}$ alkyl group, and $R^5$ is a linear or branched $C_{3-6}$ alkyl group or a phenyl group. Most preferably, $R^3$ and $R^4$ are independently selected from the group of a linear $C_{1-4}$ or branched $C_3$ or $C_4$ alkyl group, and a phenyl or benzoyl group which may optionally be substituted with one substituent selected from the group consisting of selected from a halogen atom, a nitro group, a $C_{1-4}$ alkoxy group and a —$NR^xR^y$ group wherein $R^x$ and $R^y$ independently from each other represent a $C_1$-4 alkyl group, and $R^5$ is a linear $C_{1-4}$ or branched $C_3$ or $C_4$ alkyl group.

Moreover, in a compounds of formula (III), $R^6$ represents a hydrogen atom, an organic or organometallic group, provided that when $R^6$ is a hydrogen atom, the initiator system further comprises a sensitizer compound having a light absorption maximum in the range from 300 to 600 nm.

According to a first preferred embodiment, $R^6$ represents a group of the following formula (IV):

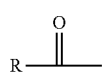

(IV)

wherein R
(i) is a group of the following formula (V):

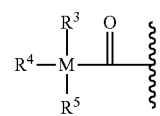

(V)

wherein M, $R^3$, $R^4$ and $R^5$ have the same meaning as defined above for formula (III), whereby the compound of formula (III) may be symmetrical or unsymmetrical; or (ii) is a group of the following formula (VI):

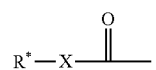

(VI)

wherein
X represents a single bond, an oxygen atom or a group NR', wherein R' represents a substituted or unsubstituted hydrocarbyl group;
R* represents a substituted or unsubstituted hydrocarbyl group, a trihydrocarbylsilyl group, a mono(hydrocarbylcarbonyl)dihydrocarbylsilyl group or a di(hydrocarbylcarbonyl)monohydrocarbylsilyl group; or
(iii) when M is Si, R may be a substituted or unsubstituted hydrocarbyl group.

For R* of formula (VII) being a trihydrocarbylsilylgroup, a mono(hydrocarbylcarbonyl)-dihydrocarbylsilyl group or a di(hydrocarbylcarbonyl)monohydrocarbylsilyl group, each of the hydrocarbyl and hydrocarbylcarbonyl groups has the same meaning as defined for $R^1$, $R^2$ and $R^3$ and is independently selected therefrom.

In formula (VI), R' has the same meaning as defined for $R^5$ and is independently selected therefrom.

According to a second preferred embodiment, $R^6$ represents a hydrogen atom. Accordingly, the initiator system further comprises a sensitizer compound. The sensitizer compound is preferably an alpha-diketone sensitizer compound having a light absorption maximum in the range from 300 to 500 nm. The alpha-diketone sensitizer is capable of absorbing visible light and forming a photoexcitation complex with a hydrogen donating compound of formula (I). The alpha-diketone photoinitiator compound may be selected from camphorquinone, 1,2-diphenylethane-1,2-dione (benzil), 1,2-cyclohexanedione, 2,3-pentanedione, 2,3-hexanedione, 3,4-hexanedione, 2,3-heptanedione, 3,4-heptanedione glyoxal, biacetyl, 3,3,6,6-tetramethylcyclohexanedione, 3,3,7,7-tetramethyl-1,2-cycloheptanedione, 3,3,8,8-tetramethyl-1,2-cyclooctanedione; 3,3,18,18-tetramethyl-1,2-cyclooctadecanedione; dipivaloyl; furil, hydroxybenzil, 2,3-butanedione, 2,3-octanedione, 4,5-octanedione, and 1-phenyl-1,2-propanedione. Camphorquinone is the most preferred alpha-diketone photoinitiator. According to a preferred embodiment, the polymerizable matrix contains the alpha-diketone sensitizer in an amount from 0.05 to 5 mole percent.

Preferably, in the compounds of formula (I), M is Si.

For example, compounds of formula (III) wherein R has the formula (VI) and which are symmetrical may be have the following structural formulae:

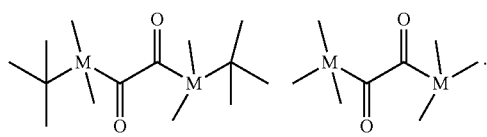

For example, compounds of formula (III) wherein R represents a group of formula (VI) wherein X is a bond, an oxygen atom or a NR' group, and R* represents a substituted or unsubstituted hydrocarbyl group may have the following structural formulae:

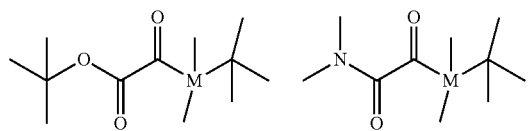
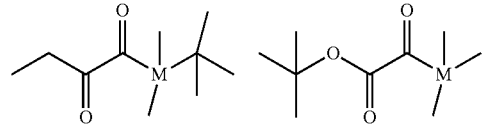
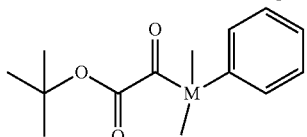
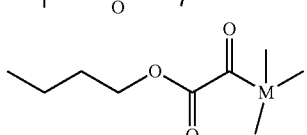
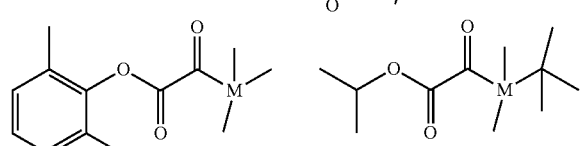
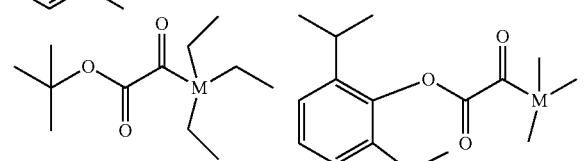
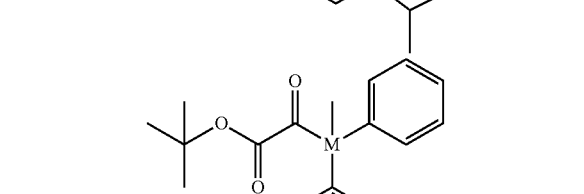
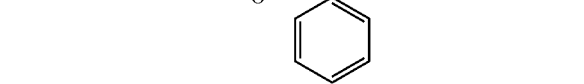
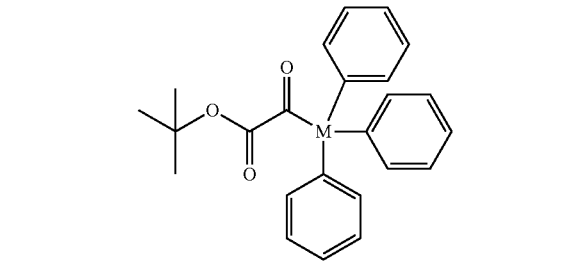

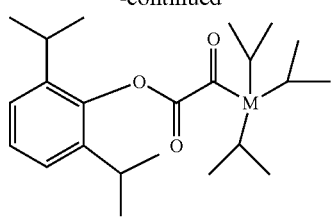
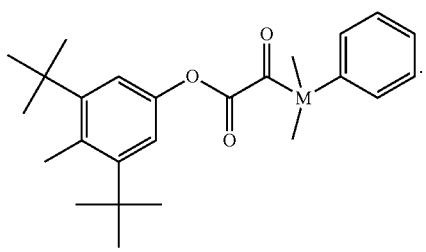

For example, compounds of formula (III) wherein R represents a group of formula (VI) wherein R* represents a trihydrocarbylsilyl group have the following structural formulae:

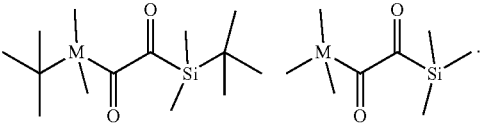

For example, compounds of formula (III) wherein M is Si and R represents a substituted or unsubstituted hydrocarbyl group may have the following structural formulae:

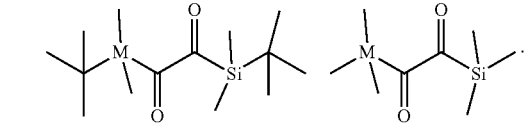
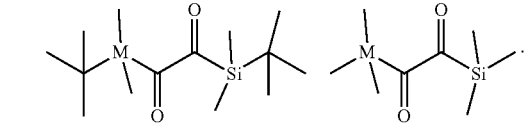
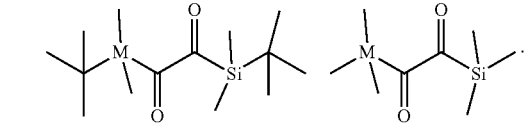
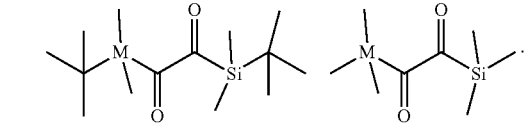
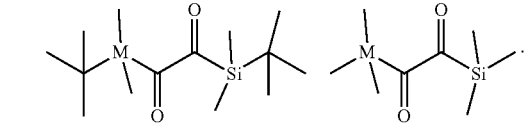
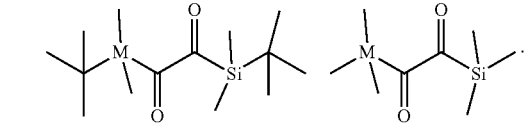
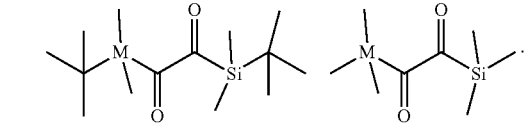
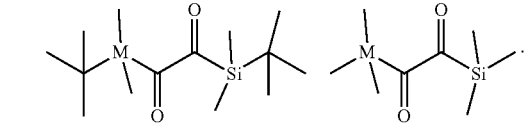
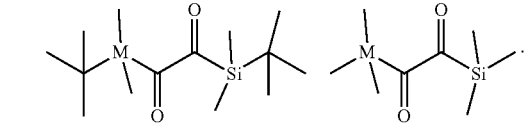
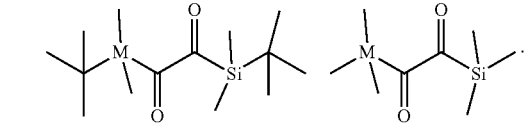
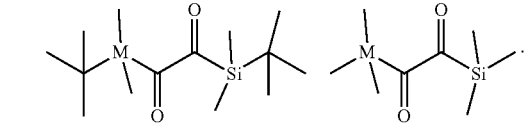

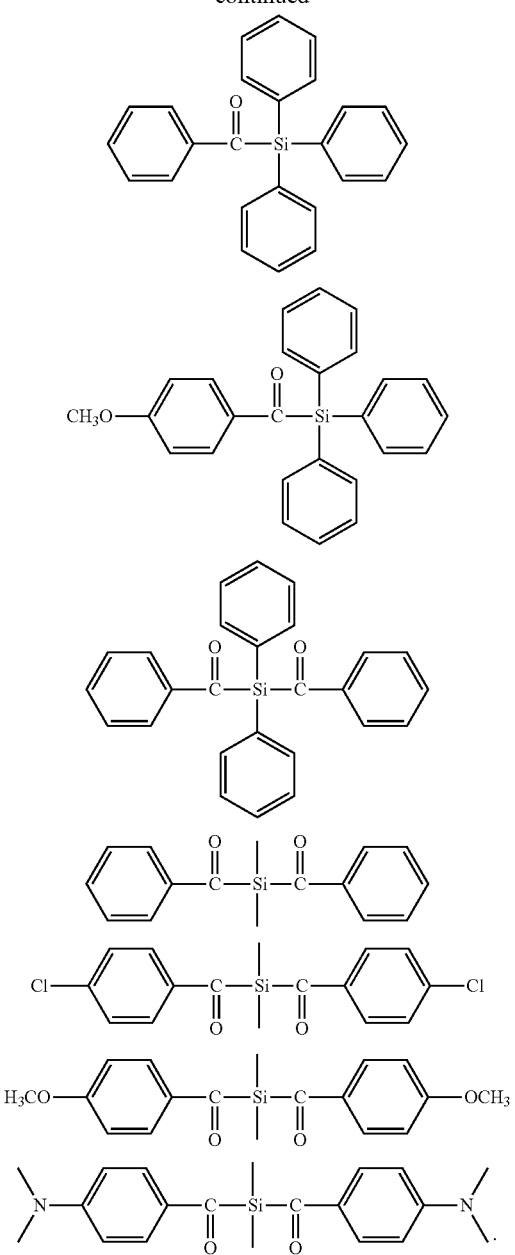

Preferably, compound of formula (III) is selected from the group consisting of:

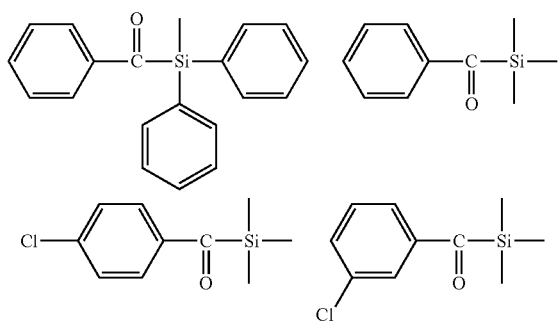

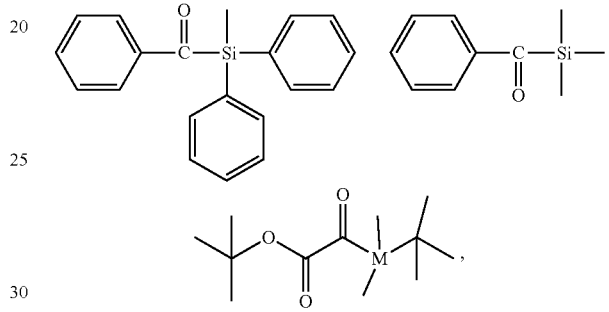

wherein compounds of formula (III) with M=Si are particularly preferred.

More preferably, compound of formula (III) is selected from the group consisting of:

wherein it is particularly preferred that M=Si.

Most preferably, compound of formula (III) is tert-butyl (tert-butyldimethylsilyl)glyoxylate) (DKSi).

A suitable photoinitiator system may also include phosphine oxides typically having a functional wavelength range of about 380 nm to about 1200 nm. Examples of phosphine oxide free radical initiators with a functional wavelength range of about 380 nm to about 450 nm include acyl and bisacyl phosphine oxides such as those described in U.S. Pat. Nos. 4,298,738, 4,324,744 and 4,385,109 and EP 0 173 567. Specific examples of the acylphosphine oxides include 2,4,6-trimethylbenzoyldiphenylphosphine oxide, bis(2,4,6-trimethylbenzoyl)phenylphosphine oxide, dibenzoylphenylphosphine oxide, bis(2,6-dimethoxybenzoyl)phenylphosphine oxide, tris(2,4-dimethylbenzoyl)phosphine oxide, tris(2-methoxybenzoyl)phosphine oxide, 2,6-dimethoxybenzoyldiphenylphosphine oxide, 2,6-dichlorobenzoyldiphenylphosphine oxide, 2,3,5,6-tetramethylbenzoyldiphenylphosphine oxide, benzoyl-bis(2,6-dimethylphenyl) phosphonate, and 2,4,6-trimethylbenzoylethoxyphenylphosphine oxide. Commercially available phosphine oxide photoinitiators capable of free-radical initiation when irradiated at wavelength ranges of greater than about 380 nm to about 450 nm include bis(2,4,6-trimethylbenzoyl)phenyl phosphine oxide (IRGACURE 819), bis(2,6-dimethoxybenzoyl)-(2,4,4-trimethylpentyl) phosphine oxide (CGI 403), a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE 1700), a 1:1 mixture, by weight, of bis(2,4,6-trimethylbenzoyl)phenyl phosphine oxide and 2-hydroxy-2-methyl-1-phenylpropane-1-one (DAROCUR 4265), and ethyl 2,4,6-trimethylbenzylphenyl phosphinate (LUCIRIN LR8893X). Typically, the phosphine oxide initiator is present in the composition in catalytically effective amounts, such as from 0.1 percent by weight to 5.0 percent by weight, based on the total weight of the composition.

Suitable electron donor compounds include substituted amines, e.g., ethyl dimethylaminobenzoate or dimethylamino benzonitrile.

Tertiary amine reducing agents may be used in combination with an acylphosphine oxide Examples of suitable aromatic tertiary amine include N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, N,N-bis(2-hydroxyethyl)-3,5-dimethylaniline, N,N-bis(2-hydroxyethyl)-p-toluidine, N,N-bis(2-hydroxyethyl)-3,4-dinnethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, 4-N,N-dimethylanninobenzoic acid ethyl ester, 4-N,N-dimethylaminobenzoic acid methyl ester, 4-N,N-dimethylaminobenzoic acid n-butoxyethyl ester, 4-N,N-dimethylaminobenzoic acid 2-(methacryloyloxy) ethyl ester, 4-N,N-dimethylaminobenzophenone ethyl 4-(N,N-dimethylamino) benzoate and N,N-dimethylaminoethyl methacrylate. Examples of an aliphatic tertiary amine include trimethylamine, triethylamine, N-methyldiethanolamine, N-ethyldiethanolamine, N-n-butyldiethanolamine, N-lauryldiethanolamine, triethanolamine, 2-(dimethylamino) ethyl methacrylate, N-methyldiethanolamine dimethacrylate, N-ethyldiethanolamine dimethacrylate, triethanolamine monomethacrylate, triethanolamine dimethacrylate, and triethanolamine trimethacrylate.

The amine reducing agent may be present in the composition in an amount from 0.1 percent by weight to 5.0 percent by weight, based on the total weight of the composition.

According to a further preferred embodiment, the photo initiator further comprises an iodonium compound of the following formula (VII):

wherein
$R^7$ and $R^8$
which are independent from each other, represent an organic moiety, and
$A^-$ is an anion;

For example, diaryl iodonium salt may be selected from (4-methylphenyl)[4-(2-methylpropyl) phenyl] iodonium hexafluoroantimonate, include (4-methylphenyl)[4-(2-methylpropyl) phenyl] iodonium tetrafluoroborate, diphenyliodonium (DPI) tetrafluoroborate, di(4-methylphenyl)iodonium (Me2-DPI) tetrafluoroborate, phenyl-4-methylphenyliodonium tetrafluoroborate, di(4-heptylphenyl)iodonium tetrafluoroborate, di(3-nitrophenyl)iodonium hexafluorophosphate, di(4-chlorophenyl)iodonium hexafluorophosphate, di(naphthyl)iodonium tetrafluoroborate, di(4-trifluoromethylphenyl)iodonium tetrafluoroborate, DPI hexafluorophosphate, Me2-DPI hexafluorophosphate; DPI hexafluoroarsenate, di(4-phenoxyphenyl)iodonium tetrafluoroborat, phenyl-2-thienyliodonium hexafluorophosphate, 3,5-dimethylpyrazolyl-4-phenyliodonium hexafluorophosphate, DPI hexafluoroantimonate, 2,2'-DPI tetrafluoroborate, di(2,4-dichlorophenyl)iodonium hexafluorophosphate, di(4-bromophenyl)iodonium hexafluorophosphate, di(4-methoxyphenyl)iodonium hexafluorophosphate, di(3-carboxyphenyl)iodonium hexafluorophosphate, di(3-methoxycarbonylphenyliodonium hexafluorophosphate, di(3-methoxysulfonylphenyl)iodonium hexafluorophosphate, di(4-acetamidophenyl)iodonium hexafluorophosphate, di(2-benzothienyl)iodonium hexafluorophosphate, and DPI hexafluorophosphate.

Particularly preferred iodonium compounds include diphenyliodonium (DPI) hexafluorophosphate, di(4-methylphenyl)iodonium (Me2-DPI) hexafluorophosphate, diaryliodonium hexafluoroantimonate, (4-methylphenyl)[4-(2-methylpropyl) phenyl] iodonium hexafluoroantimonate, (4-methylphenyl)[4-(2-methylpropyl)phenyl]iodonium hexafluorophosphate (Irgacure® 250, commercial product available from BASF SE), (4-methylphenyl)[4-(2-methylpropyl) phenyl] iodonium tetrafluoroborate, 4-octyloxyphenyl phenyliodonium hexafluoroantimonate, 4-(2-hydroxytetradecyloxyphenyl)phenyliodonium hexafluoroantimonate, and 4-isopropyl-4'-methyldiphenyliodonium borate.

According to a particularly preferred embodiment, the iodonium compound is DPI hexafluorophosphate and/or 4-isopropyl-4'-methyldiphenyliodonium tetrakis(pentafluorophenyl) borate.

According to a further preferred embodiment, the photo initiator further comprises a sulfonium compound of the following formula (IV):

wherein
$R^9$, $R^{10}$ and $R^{11}$
which are independent from each other, represent an organic moiety or wherein any two of $R^9$, $R^{10}$ and $R^{11}$ form a cyclic structure together with the sulfur atom to which they are bound, and
$A^-$ is an anion.

A preferred triaryl sulfonium salt is S-(phenyl)thianthrenium hexafluorophosphate:

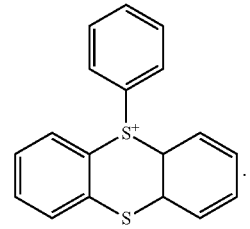

According to a further preferred embodiment, the photo initiator further comprises a phosphonium compound of the following formula (V):

wherein
$R^{12}$, $R^{13}$, $R^{14}$, and $R^{15}$
which are independent from each other, represent an organic moiety, and
$A^-$ is an anion.

Particularly preferred phosphonium salts are the tetraalkyl phosphonium salts tetrakis-(hydroxymethyl)-phosphonium (THP) salt or a tetrakis-(hydroxymethyl)-phosphonium hydroxide (THPOH) salt, wherein the anion of the tetraalkyl phosphonium salt is selected from the group consisting of formate, acetate, phosphate, sulphate, fluoride, chloride, bromide and iodide.

Optional Polymerizable (Meth)Acrylates or (Meth)Acrylamides

The dental impression material of the present invention may further comprise which up to 20 percent by weight based on the total weight of the composition of polymerizable (meth)acrylates or (meth)acrylamides.

The (meth)acrylate compounds may be selected from methyl acrylate, methyl methacrylate, ethyl acrylate, ethyl methacrylate, propyl acrylate, propyl methacrylate, isopropyl acrylate, isopropyl methacrylate, 2-hydroxyethyl acrylate, 2-hydroxyethyl methacrylate (HEMA), hydroxypropyl acrylate, hydroxypropyl methacrylate, tetrahydrofurfuryl acrylate, tetrahydrofurfuryl methacrylate, glycidyl acrylate, glycidyl methacrylate, bisphenol A glycerolate dimethacrylat ("bis-GMA", CAS-No. 1565-94-2), 4,4,6,16 (or 4,6,6,16)-tetramethyl-10,15-dioxo-11,14-dioxa-2,9-diazaheptadec-16-enoicacid 2-[(2-methyl-1-oxo-2-propen-1-yl)oxy] ethyl ester (CAS no. 72869-86-4)_(UDMA), glycerol mono- and di-acrylate such as 1,3-glycerol dimethacrylate (GDM), glycerol mono- and dimethacrylate, ethyleneglycol diacrylate, ethyleneglycol dimethacrylate, polyethyleneglycol diacrylate (where the number of repeating ethylene oxide units vary from 2 to 30), polyethyleneglycol dimethacrylate (where the number of repeating ethylene oxide units vary from 2 to 30 especially triethylene glycol dimethacrylate ("TEGDMA"), neopentyl glycol diacrylate, neopentylglycol dimethacrylate, trimethylolpropane triacrylate, trimethylol propane trimethacrylate, mono-, di-, tri-, and tetra-acrylates and methacrylates of pentaerythritol and dipentaerythritol, 1,3-butanediol diacrylate, 1,3-butanediol dimethacrylate, 1,4-butanedioldiacrylate, 1,4-butanediol dimethacrylate, 1,6-hexane diol diacrylate, 1,6-hexanediol dimethacrylate, di-2-methacryloyloxethyl hexamethylene dicarbamate, di-2-methacryloyloxyethyl trimethylhexanethylene dicarbamate, di-2-methacryloyl oxyethyl dimethylbenzene dicarbamate, methylene-bis-2-methacryloxyethyl-4-cyclohexyl carbamate, di-2-methacryloxyethyl-dimethylcyclohexane dicarbamate, methylene-bis-2-methacryloxyethyl-4-cyclohexyl carbamate, di-1-methyl-2-methacryloxyethyl-trimethylhexamethylene dicarbamate, di-1-methyl-2-methacryloxyethyl-dimethylbenzene dicarbamate, di-1-methyl-2-methacryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-2-methacryloxyethyl-4-cyclohexyl carbamate, di-1-methyl-2-methacryloxyethyl-hexamethylene dicarbamate, di-1-methyl-2-methacryloxyethyl-trimethylhexamethylene dicarbamate, di-1-methyl-2-methacryloxyethyl-dimethylbenzene dicarbamate, di-1-methyl-2-metha-cryloxyethyl-dimethylcyclohexane dicarbamate, methylene-bis-1-methyl-2-methacryloxyethyl-4-cyclohexyl carbamate, di-1-chloromethyl-2-methacryloxyethyl-hexamethylene dicarbamate, di-1-chloromethyl-2-methacryloxyethyl-trimethylhexamethylene dicarbamate, di-1-chloromethyl-2-methacryloxyethyl-dimethylbenzene dicarbamate, di-1-chloromethyl-2-methacryloxyethyl-dimethylcyclohexane dicarbamate, methylene-bis-1-chloromethyl-2-methacryloxyethyl 4-cyclohexyl carbamate, 2,2'-bis(4-methacryloxyphenyl)propane, 2,2'bis(4-acryloxyphenyl)propane, 2,2'-bis[4(2-hydroxy-3-methacryloxy-phenyl)]propane, 2,2'-bis[4(2-hydroxy-3-acryloxy-phenyl)propane, 2,2'-bis(4-methacryloxyethoxyphenyl)propane, 2,2'-bis(4-acrylox- yethoxyphenyl)propane, 2,2'-bis(4-methacryloxypropoxyphenyl)propane, 2,2'-bis(4-acryloxypropoxyphenyl)propane, 2,2'-bis(4-methacryloxydiethoxyphenyl)propane, 2,2'-bis(4-acryloxydiethoxyphenyl)propane, 2,2'-bis[3(4-phenoxy)-2-hydroxypropane-1-methacrylate]propane, and 2,2'-bis[3(4-phenoxy)-2-hydroxypropane-1-acrylate]propane.

Preferred (meth)acrylamides may be selected from the following compounds.

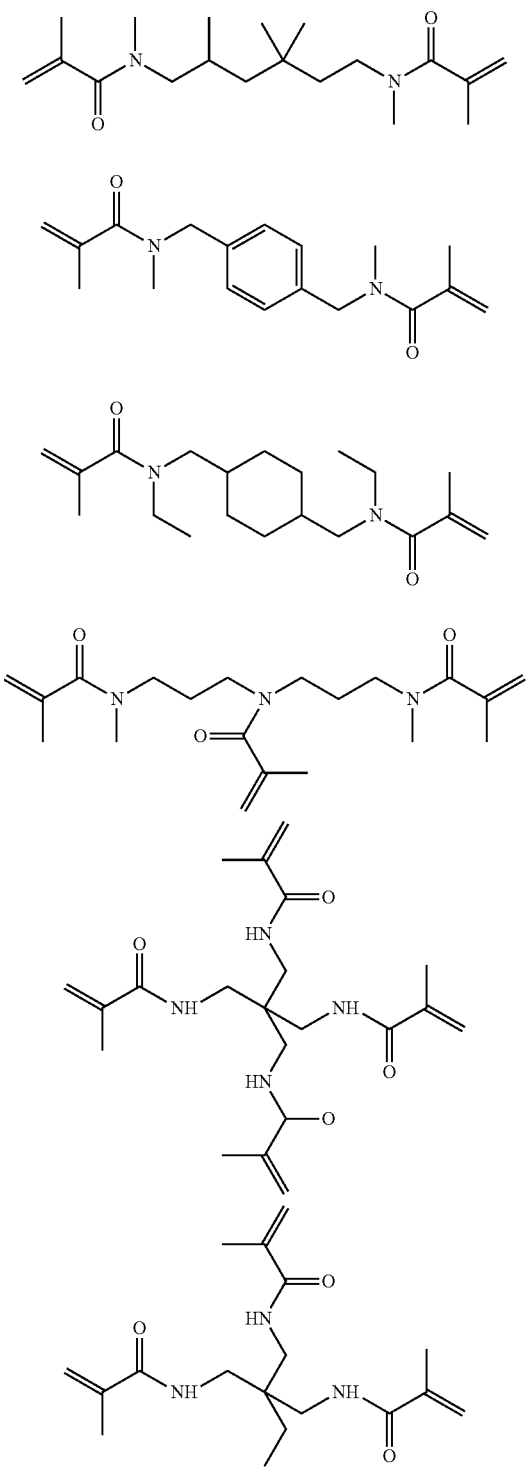

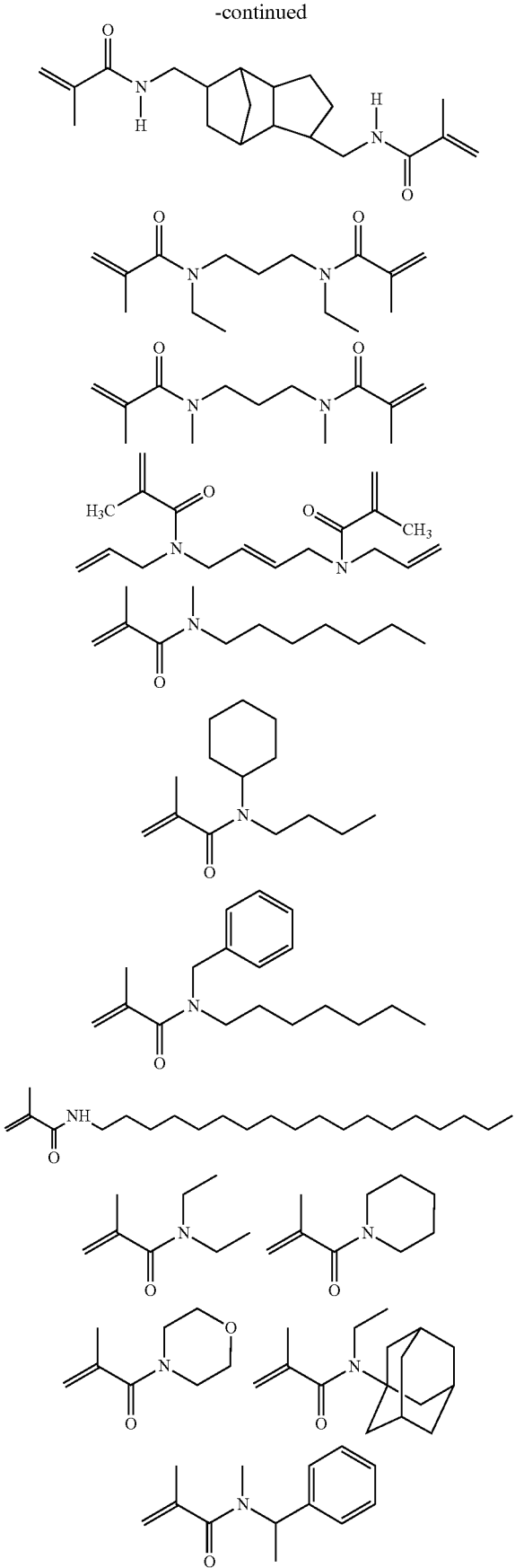
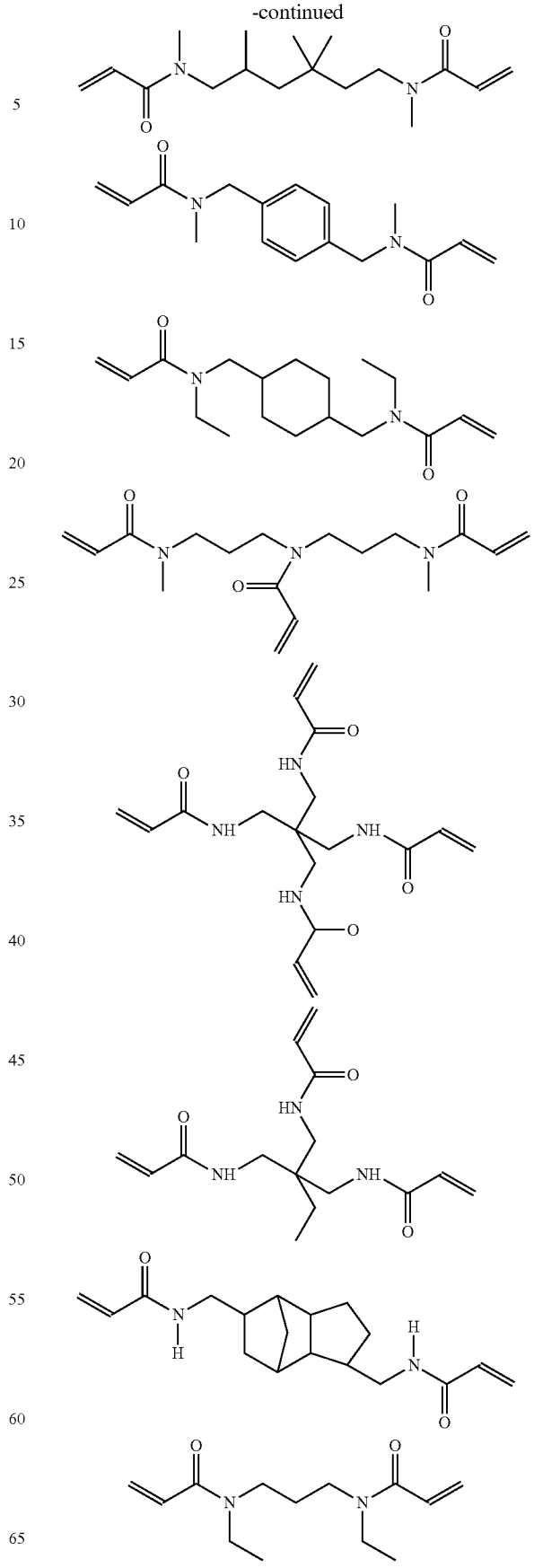

21
-continued
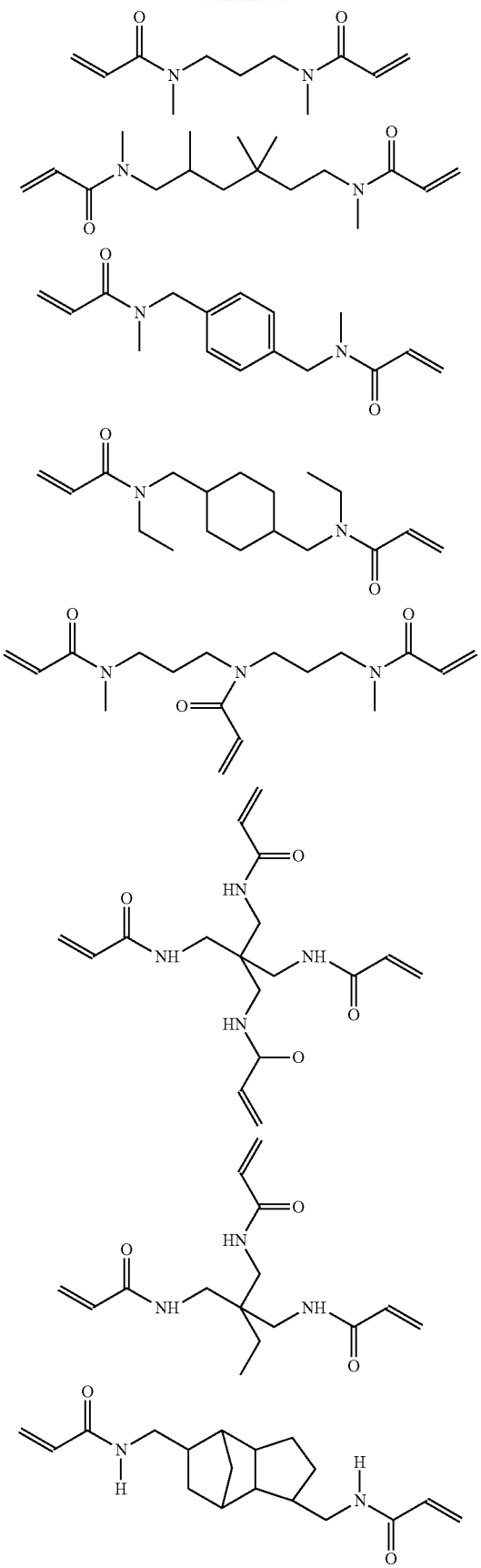
22
-continued
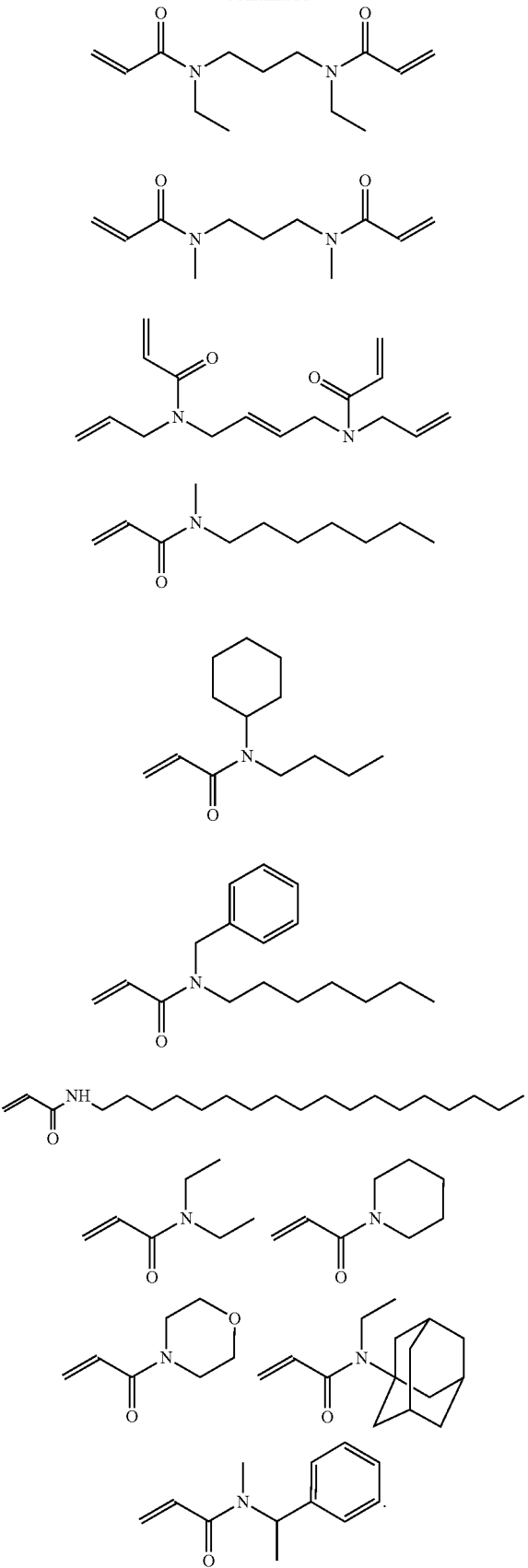

Most preferred are the bis-(meth)acrylamides:
N,N'-diallyl-1,4-bisacrylamido-(2E)-but-2-en (BAABE) having the structural formula

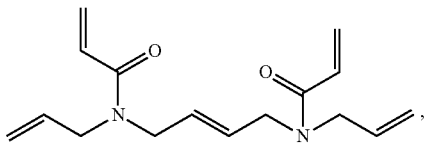 [SMILES: C=CCN(C/C=C/CN(CC=C)C(=O)C=C)C(=O)C=C]

and

N,N'-diethyl-1,3-bisacrylamido-propan (BADEP) having the structural formula

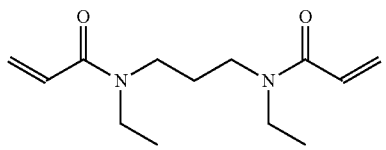 [SMILES: C=CC(=O)N(CC)CCCN(CC)C(=O)C=C]

Further Components

Optionally, the dental impression material of the present invention may further comprise stabilizer(s), and/or pigments. Moreover, the dental impression material of the present invention may further comprise cationically polymerizable monomers.

The term "stabilizer" as used herein means any compound capable of preventing polymerizable compounds contained in the dental impression material from spontaneous polymerization during storage. However, the stabilizer does not disturb or prevent intended polymerisation curing of the dental impression material during application.

For example, the stabilizer may be a conventional stabilizer selected from the group consisting of hydroquinone, hydroquinone monomethylether, tert-butyl-hydroquinone, tert-butylhydroxyanisol, propyl gallate and 2,6-di-tert-butyl-p-cresol. From these conventional stabilizers, 2,6-di-tert-butyl-p-cresol is preferred.

The dental impression material according to the invention may contain the stabilizer in an amount of 0.001 to 1 percent by weight, preferably 0.005 to 0.8 percent by weight based on the total weight of the composition. When the amount of the stabilizer is below the above indicated lower limit of 0.001, then storage stability of the dental impression material might be insufficient, since the amount of stabilizer is too small to provide a stabilizing effect. However, when the amount of stabilizer is above the maximum threshold of 1 percent by weight, then the applicability of the dental impression material might be negatively affected, since higher amounts of stabilizer may disturb or even substantially prevent intended polymerization curing of the dental impression material during application.

According to a specific embodiment, the dental impression material according to the invention may comprise a compound having one or more cationic polymerizable groups, according to the following formula (VI).

(VI)

wherein
K=cationically polymerizable group
$R^{24}$=organic moiety
$o \geq 1$

Preferably, K represents a vinyl ether group, a vinyl ester group, a vinyl siloxane group, an epoxide group, an oxetane group and a furane group.

More preferably, K represents a vinyl ether group and a vinyl ester group, most preferably K represents a vinyl ether group.

Preferably, $R^{24}$ represents an o-valent $C_{1-30}$ hydrocarbyl groups which may contain 1-15 heteroatoms selected from O, S, Si, and which may be substituted by 1-15 substituents selected from $C_{1-4}$ alkyl groups, $C_{4-10}$ aryl groups, $C_{4-9}$ heteroaryl groups, halogen atoms, $C_{1-4}$ alkoxy groups, ester groups, thioether groups, silyl groups, and siloxane groups.

The hydrocarbyl group may be an alkyl group, a cycloalkyl group, a cycloalkylalkyl group, an arylalkyl group or an aryl group.

An alkyl group may be straight-chain or branched $C_{1-3}$ alkyl group, typically a $C_{1-6}$ alkyl group. Examples for a $C_{1-6}$ alkyl group can include linear or branched alkyl groups having 1 to 6 carbon atoms, preferably 1 to 4 carbon atoms, for example, methyl, ethyl, n-propyl, isopropyl, n-butyl, isobutyl, sec-butyl, tert-butyl, n-pentyl, isopentyl and n-hexyl.

A cycloalkyl group may be a $C_{3-20}$ cycloalkyl group, typically a $C_{3-8}$ cycloalkyl group. Examples of the cycloalkyl group can include those having 3 to 6 carbon atoms, for example, cyclopropyl, cyclobutyl, cyclopentyl and cyclohexyl.

A cycloalkylalkyl group may have 4 to 20 carbon atoms and may include a combination of a linear or branched alkyl group having 1 to 6 carbon atoms and a cycloalkyl group having 3 to 14 carbon atoms. Examples of the cycloalkylalkyl group can for example, include methylcyclopropyl, methylcyclobutyl, methylcyclopentyl, methylcyclohexyl, ethylcyclopropyl, ethylcyclobutyl, ethylcyclopentyl, ethylcyclohexyl, propylcyclopropyl, propylcyclobutyl, propylcyclopentyl, propylcyclohexyl.

An arylalkyl group may be a $C_{7-20}$ arylalkyl group, typically a combination of a linear or branched alkyl group having 1 to 6 carbon atoms and an aryl group having 6 to 10 carbon atoms. Specific examples of an arylalkyl group are a benzyl group or a phenylethyl group.

An aryl group can include aryl groups having 6 to 10 carbon atoms. Examples of the aryl group are phenyl and naphtyl.

The hydrocarbylcarbonyl groups of $R^{24}$ represent acyl groups ($R^{25}$—(C=O)—) in which the organic residue $R^{25}$ is a hydrocarbyl residue as defined above.

Preferably, the hydrocarbylcarbonyl group is an arylcarbonyl group, more preferably a benzoyl group.

Preferably, $R^{24}$ is selected from the group consisting of a straight chain or branched $C_{1-6}$ alkyl group, and a phenyl or benzoyl group which may optionally be substituted by one to three substitutents selected from halogen atoms, $C_{1-4}$ alkoxy groups.

Preferably, o is between 1 and 4, more preferably o is 2.

More preferably, the reactive diluent is a compound of the formula (XII)

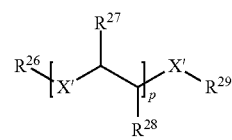

(XII)

wherein $R^{26}$ and $R^{29}$
which may be the same or different, independently represent a hydrogen atom, a $C_{1-4}$ alkyl group, a vinyl group, a vinyl silyl group, an epoxide group, an oxetane group, a furane group, $R^{27}$ and $R^{28}$
which may be the same or different, independently represent a hydrogen atom, a $C_{1-4}$ alkyl group, or a vinyl ether group, a vinyl ester group, a vinyl siloxane group, an epoxide group, an oxetane group, a furane group, X' represents an oxygen, a sulfur or a carbon atom, p represents an integer of from 1 to 10, provided that at least one cationic polymerizable group is present in the compound of formula (XII).

In a preferable embodiment, X' represents an oxygen atom, $R^{27}$ represents a hydrogen atom, or a methyl group, $R^{28}$ represents a hydrogen atom, $R^{26}$ and $R^{29}$ represent vinyl groups, more preferable X' represents an oxygen atom, $R^{27}$ and $R^{28}$ represent a hydrogen atom, $R^{26}$ and $R^{28}$ represent vinyl groups.

A particular suitable reactive diluent is ethylene glycol vinyl ether.

The present invention provides a method for preparing a dental impression.

The method comprises providing a curable dental impression material according to the present invention.

Moreover, the method further comprises taking an impression of a dental structure.

Finally, the method of the present invention comprises curing the dental impression material with light having a wavelength in the range of 200 to 800 nm.

The present invention also provides the use of the photocurable dental impression material according to the present invention for the preparation of a dental impression.

The present invention will now be further illustrated based on the following examples.

EXAMPLES

The compounds investigated to develop photoinitiating systems are given in Scheme 1. The monomers used for radical polymerization are given in Scheme 2. All these chemical compounds are commercially available and were used with the highest purity available.

1) Initiators and Additives

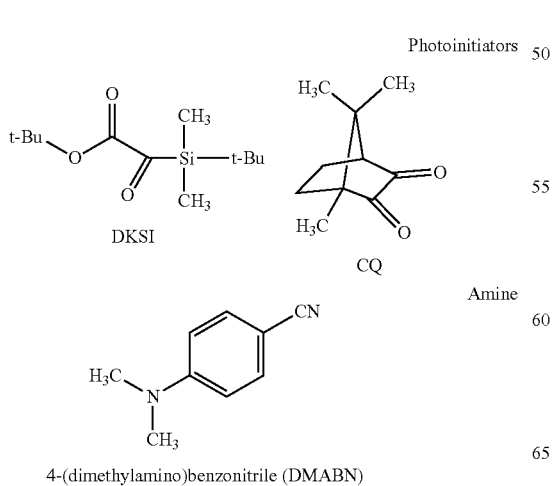

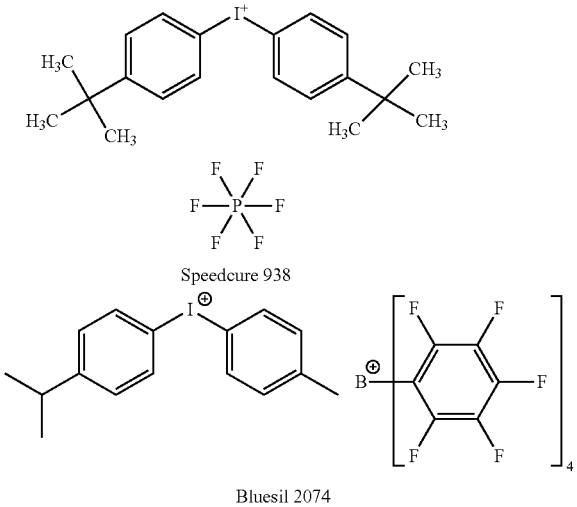

Scheme 1. Exemplary Photoinitiators (DKSi and CQ) and Co-Initiator (DMABN) or Iodonium Salt 2) Silicone-Acrylates (Radical Polymerization)

Scheme 2A. Exemplary Radical Monomers (Silicone-(Meth)Acrylates)

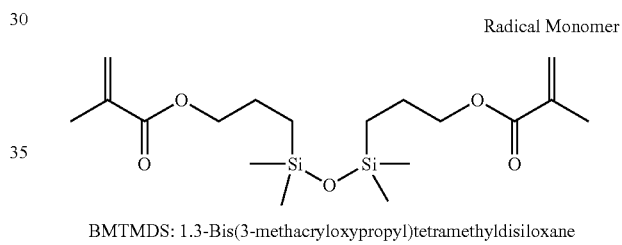

BMTMDS: 1.3-Bis(3-methacryloxypropyl)tetramethyldisiloxane

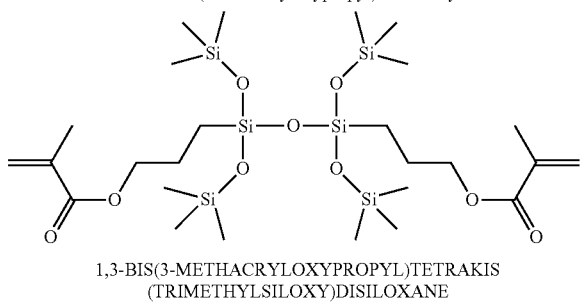

1,3-BIS(3-METHACRYLOXYPROPYL)TETRAKIS (TRIMETHYLSILOXY)DISILOXANE

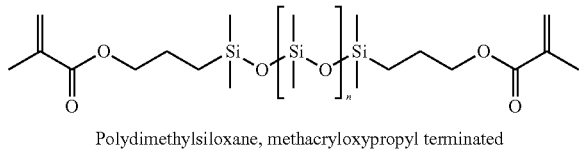

Polydimethylsiloxane, methacryloxypropyl terminated

Figure 2:
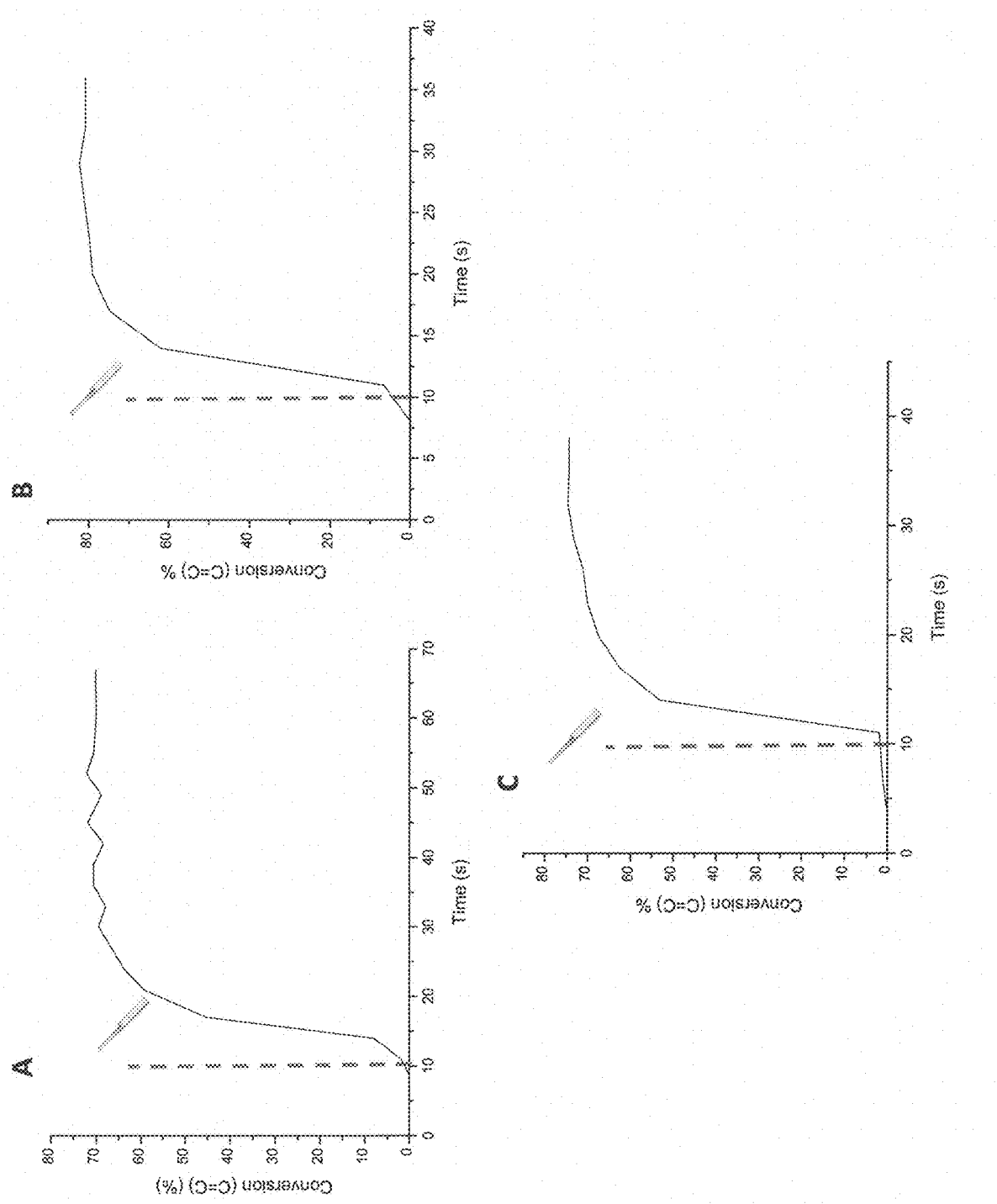
FIG. 2 shows photopolymerization profiles of (meth) acrylate function for (A) PRO21536 using DKSi 2% (w/w) as photoinitiating system; (B) PRO21536/urethane dimethacrylate (UDMA) (57/43% w/w) using CQ/DMABN (1/1% w/w) and (C) PRO21536/CN9800 (75%/25% w/w) using CQ/DMABN (1/1% w/w) (under air; thickness=1.4 mm; Smartlite Focus 300 mW·cm$^{-2}$).

CN9800: difunctional aliphatic silicone acrylate oligomer from Sartomer
PRO21536: hexafunctional silicone urethane acrylate from Sartomer Example 1. Radical Polymerization of Silicone-Acrylates DKSi is a photoinitiator bearing a Si atom and exhibits an excellent solubility in silicones. Different initiating systems based on camphorquinone/amine (and optionally Iodonium salt) or DKSi (and optionally amine and iodonium salt) were used to initiate the polymerization of silicone acrylates (FIGS. 1 and 2). Remarkably, excellent polymerization profiles were obtained for DKSi or CQ based initiating systems upon blue light and under air showing their high performance. Tack free polymers can be obtained. Remarkably, the presence of iodonium salt is not required for high performance system (See FIG. 1C for CQ/amine vs. CQ/amine/iodonium). Excellent final conversions are reached under air and for samples of thickness 1.4 mm for a Dental LED ($\lambda_{max}$~480 nm). Without initiating system (i.e. CQ or DKSi), no polymerization occurs. Moreover, the bleaching properties are found excellent in presence of DKSi. Some blends urethane acrylate (UDMA) with silicone acrylate (PRO21536) are also possible leading to excellent photopolymerization profiles (FIG. 2B).

Figure 3:
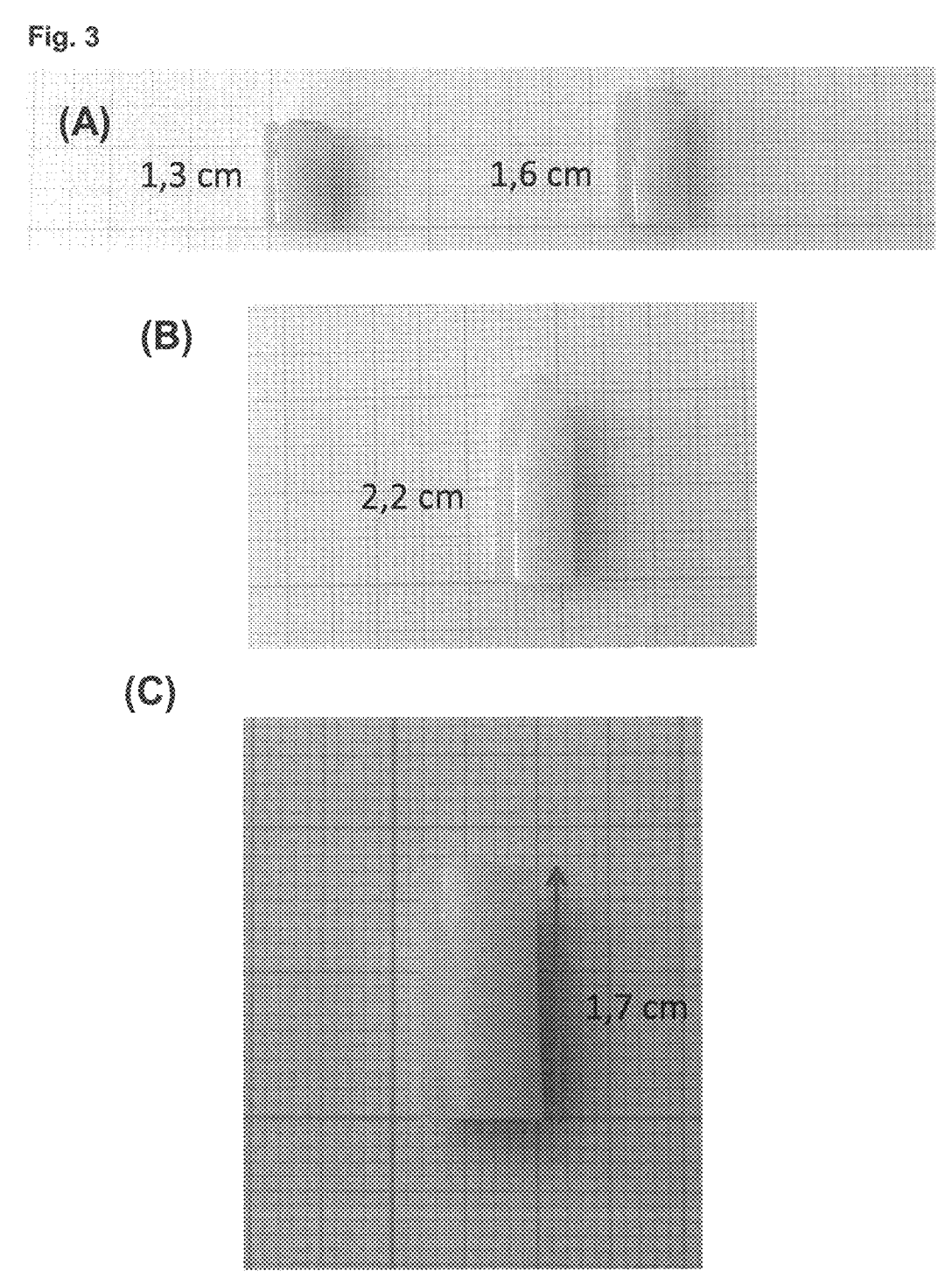
Figure 4:
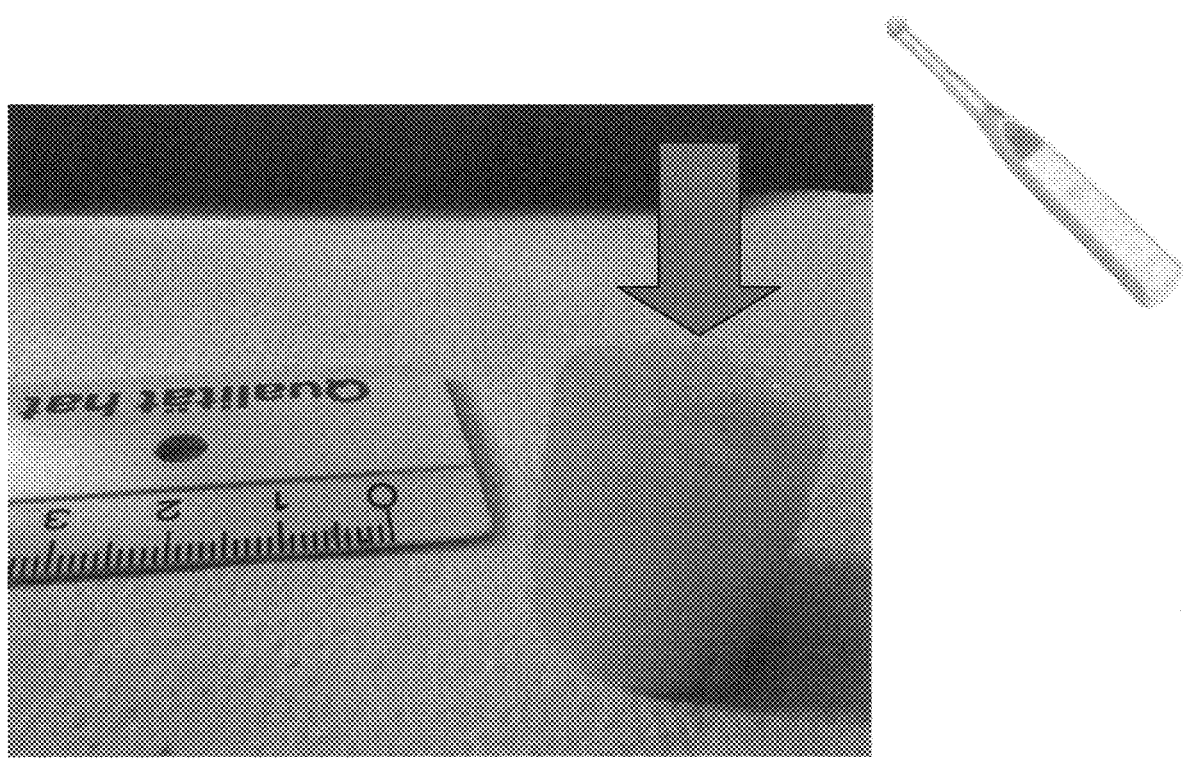
FIG. 4 shows depth of cure for the polymerization upon blue light (SmartLite Focus) of PRO21536/SDI Glass (89/ 11% w/w) using CQ/DMABN (1%/1% w/w) as photoinitiating system 60 s of irradiation (under air).
Figure 5:
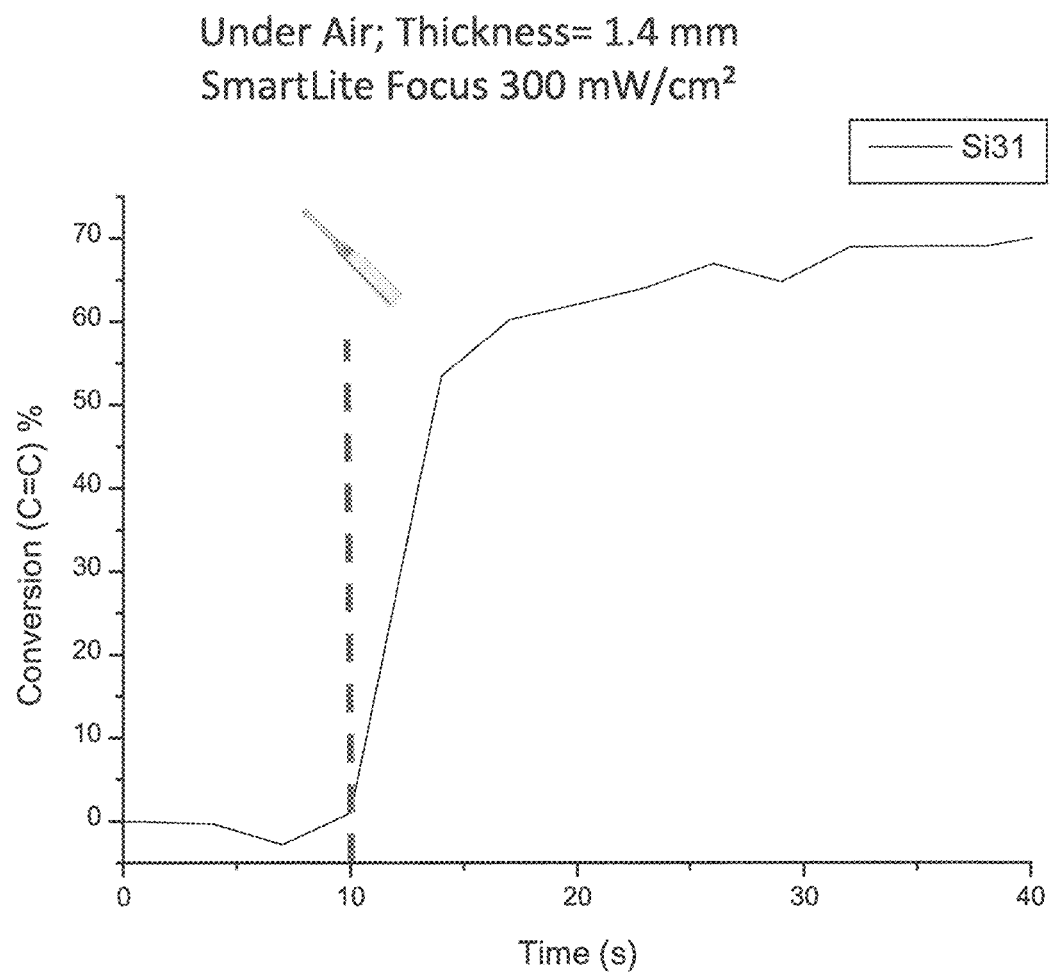
FIG. 5 shows photopolymerization profiles of (meth) acrylate function for PRO21536/SDI Glass (89/11% w/w) using CQ/DMABN (1%/1% w/w) as photoinitiating system (under air; thickness=1.4 mm; Smartlite Focus 300 mW·cm$^{-2}$).

Example 2. Depth of Cure Upon Blue Light for Silicone-Acrylates Photopolymerization For the CQ or DKSi based systems presented in the example 1, excellent depth of cure (DoC) (1-2 cm) can be observed (FIGS. 3 and 4) for the photopolymerization of silicone-acrylates. In presence of fillers (SDI Glass), high DoCs are also obtained (FIG. 3C and FIG. 4). Remarkably, in FIG. 5, the photopolymerization profile in presence of fillers is found excellent with a full curing after less than 20 s (very high polymerization rate and final acrylate conversion>70%).

Example 3. Other Silicone-Acrylates for Blue Light Photopolymerization

Figure 6:
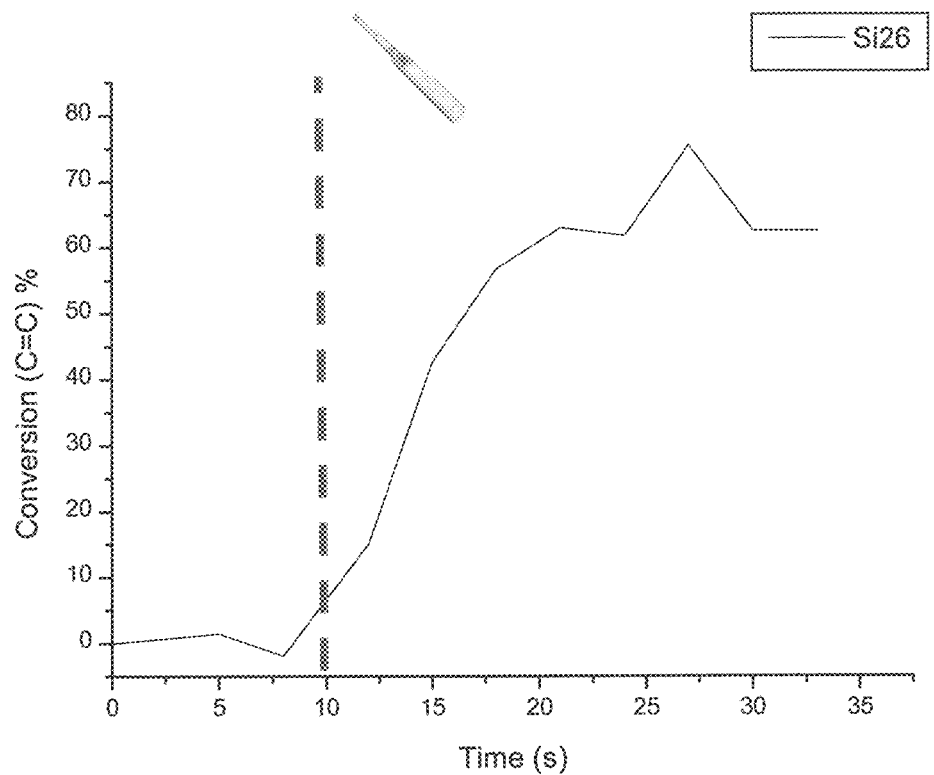
FIG. 6 shows photopolymerization profiles of (meth) acrylate function in PRO21536/1,3-BIS(3-METHACRYLOXYPROPYL)TETRAKIS (TRIMETHYLSILOXY) DISILOXANE (80/20% w/w) using CQ/DMABN (1.2%/ 1.2% w/w) as photoinitiating system (under air; thickness=1.4 mm; Smartlite Focus 300 mW·cm$^{-2}$).
Figure 7:
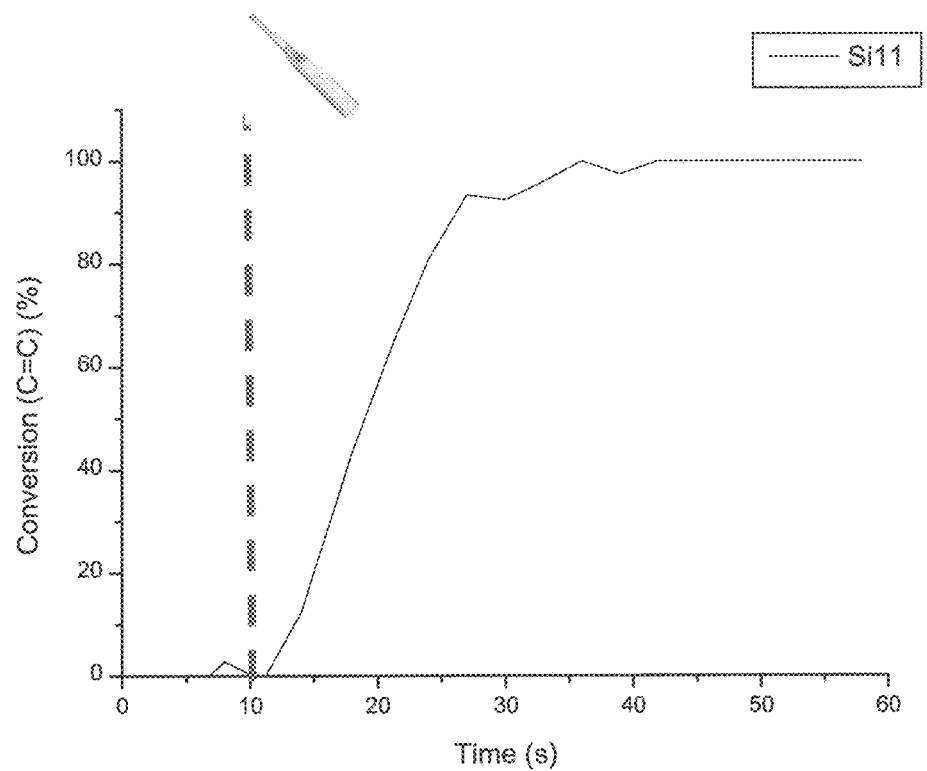
FIG. 7 shows photopolymerization profiles of (meth) acrylate function in CN9800/Polydimethylsiloxane, methacryloxypropyl terminated (74%/26% w/w) using DKSi (1.1% w/w) as photoinitiating system (under air; thickness=1.4 mm; Smartlite Focus 300 mW·cm$^{-2}$).

Remarkably, excellent polymerization profiles were obtained for DKSi or CQ based initiating systems using other monomers or oligomers in silicone-acrylates (e.g. 1,3-BIS(3-METHACRYLOXYPROPYL)TETRAKIS (TRIMETHYLSILOXY)DISILOXANE or Polydimethylsiloxane, methacryloxypropyl terminated—Scheme 2). Indeed, upon blue light and under air, excellent polymerization profiles were recorded (FIGS. 6&7). Tack free polymers can be obtained.

The invention claimed is:

1. A photocurable dental impression material comprising:
(a) a mixture of polymerizable silicone compounds each having two or more polymerizable (meth)acrylate groups, said mixture having a dynamic viscosity at 25° C. of from 1 to 100 Pas;
(b) a filler;
(c) a photo initiator system,
wherein the mixture of polymerizable silicone compounds comprises based on the total weight of the mixture of polymerizable silicone compounds
(i) 10 to 90 percent by weight of high-molecular polymerizable silicone compounds having a molecular weight in the range of from more than 4000 up to 10,000; and
(ii) 90 to 10 percent by weight of polymerizable silicone compounds having a molecular weight in the range of from 300 to 4000,
wherein a ratio of (meth)acrylate groups per total molecular weight of the polymerizable silicone compounds of (ii) is higher than a ratio of (meth)acrylate groups per total molecular weight of molecules of the high-molecular weight polymerizable silicone compounds of (i).

2. The photocurable dental impression material according to claim 1, which further comprises up to 20 percent by weight based on the total weight of the composition of polymerizable (meth)acrylates or (meth)acrylamides.

3. The photocurable dental impression material according to claim 1, wherein the polymerizable silicone compounds are compounds of the following formula (I):

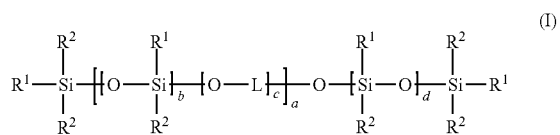

wherein
$R^1$ represents a (meth)acrylate group containing organic residue, a $C_{1-4}$ alkyl group, a group of the formula [—OSiR'$_2$]$_n$R', or two groups $R^1$ or a group $R^1$ and $R^2$ form together a group [—OSiR'$_2$]$_n$—, wherein the R', which may be the same or different, independently represent a $C_{1-4}$ alkyl group or an (meth)acrylate group containing organic residue and n is an integer of from 1 to 20;
$R^2$ represents a $C_{1-4}$ alkyl group or a group of the formula [—OSiR"$_2$]$_m$R", or two groups $R^2$ or a group $R^1$ and $R^2$ form together a group [—OSiR"$_2$]$_m$—, wherein the R", which may be the same or different, independently represent a $C_{1-4}$ alkyl group and m is an integer of from 1 to 20;
L represents a divalent $C_{1-20}$ organic linker group;
a represents 0 or an integer of from 1 to 20;
b represents 0 or an integer of from 1 to 20;
c represents 0 or an integer of from 1 to 20;
d represents 0 or an integer of from 1 to 20;
provided that at least two (meth)acrylate groups are present in the compound of formula (I).

4. The photocurable dental impression material according to claim 3, wherein $R^1$ is a group of the following formula (II)

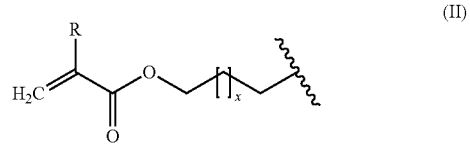

wherein
R represents a hydrogen atom or a methyl group; and
x is 0 or an integer of from 1 to 8.

5. The photocurable dental impression material according to claim 1, wherein the mixture of polymerizable silicone compounds each having two or more polymerizable (meth) acrylate groups comprises 1,3-Bis(3-methacryloxypropyl) tetramethyldisiloxane (BMTMDS), 1,3-bis(3-methacyloxypropyl)tetrakis(trimethylsiloxy)disiloxane, methacryloxypropyl terminated polydimethylsiloxane, a difunctional aliphatic silicone acrylate, and/or a hexafunctional silicone urethane acrylate.

6. The photocurable dental impression material according to claim 1, wherein the photo initiator comprises a sensitizer having an absorption maximum in the range of from 400 to 800 nm.

7. The curable dental impression material according to claim 1, wherein the photo initiator further comprises:

(1) an iodonium compound of the following formula (III):

$$R^7\text{—}I^+\text{—}R^8 A^-  \qquad (VII)$$

wherein
R$^7$ and R$^8$
which are independent from each other, represent an organic moiety, and
A$^-$ is an anion;

(2) a sulfonium compound of the following formula (IV):

$$R^9 R^{10} R^{11} S^+ A^- \qquad (IV)$$

wherein
R$^9$, R$^{10}$ and R$^{11}$
which are independent from each other, represent an organic moiety or wherein any two of R$^9$, R$^{10}$ and R$^{11}$ form a cyclic structure together with the sulfur atom to which they are bound, and
A$^-$ is an anion; and/or (3) a phosphonium compound of the following formula (V):

$$R^{12} R^{13} R^{14} R^{15} P^+ A^- \qquad (V)$$

wherein
R$^{12}$, R$^{13}$, R$^{14}$, and R$^{15}$
which are independent from each other, represent an organic moiety, and
A$^-$ is an anion.

8. The photocurable dental impression material according to claim 1, which comprises 40 to 90 percent by weight based on the total weight of the dental impression material of mixture of polymerizable silicone compounds each having two or more polymerizable (meth)acrylate groups.

9. The photocurable dental impression material according to claim 1, which comprises 10 to 60 percent by weight based on the total weight of the dental impression material of a filler.

10. The curable dental impression material according to claim 1, wherein the filler has a mean particle size in the range of from 0.05 to 5 μm.

11. The curable dental impression material according to claim 1, wherein the curable dental impression material is a one-pack composition packaged in a syringe or provided on a ready-to-use dental impression tray.

12. The photocurable dental impression material according to claim 1, wherein the mixture of polymerizable silicone compounds has a dynamic viscosity at 25° C. of from 5 to 80 Pas.

13. The photocurable dental impression material according to claim 12, wherein the mixture of polymerizable silicone compounds has a dynamic viscosity at 25° C. of from 10 to 70 Pas.

14. The photocurable dental impression material according to claim 1, wherein the mixture of polymerizable silicone compounds comprises based on the total weight of the mixture of polymerizable silicone compounds (i) 50 to 85 percent by weight of polymerizable silicone compounds having a molecular weight in the range of from more than 4000 up to 10,000; and (ii) 15 to 50 percent by weight of polymerizable silicone compounds having a molecular weight in the range of from 300 to 4000.

15. The photocurable dental impression material according to claim 1, wherein the polymerizable silicone compounds of paragraph (i) comprise either or both of 1,3-bis(3-methacryloxypropyl)tetramethyldisiloxane (BMTMDS) and 1,3-bis(3-methacyloxypropyl)tetrakis(trimethylsiloxy)disiloxane.

16. The photocurable dental impression material according to claim 1, wherein the polymerizable silicone compounds of paragraph (ii) comprise a difunctional aliphatic silicone acrylate.

17. The photocurable dental impression material according to claim 1, wherein the photo initiator comprises camphorquinone or tert-butyl(tert-butyldimethylsilyl)glyoxylate.

18. A method for preparing a dental impression, which method comprises (a) providing a curable dental impression material according to claim 1;
(b) taking an impression of a dental structure; and
(c) curing the dental impression material with light having a wavelength in the range of 200 to 800 nm.

* * * * *